United States Patent
Sattler et al.

(10) Patent No.: US 10,155,987 B2
(45) Date of Patent: Dec. 18, 2018

(54) METHODS OF PREDICTING RESISTANCE TO JAK INHIBITOR THERAPY

(71) Applicant: Dana-Farber Cancer Institute, Inc., Boston, MA (US)

(72) Inventors: Martin Sattler, Westwood, MA (US); Anagha Deshpande, Cambridge, MA (US); James D. Griffin, Needham, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/916,169

(22) Filed: Jun. 12, 2013

(65) Prior Publication Data

US 2014/0004516 A1    Jan. 2, 2014

Related U.S. Application Data

(60) Provisional application No. 61/658,711, filed on Jun. 12, 2012.

(51) Int. Cl.
| | | |
|---|---|---|
| C07H 21/04 | (2006.01) | |
| C12Q 1/68 | (2018.01) | |
| C12Q 1/6886 | (2018.01) | |
| G01N 33/574 | (2006.01) | |

(52) U.S. Cl.
CPC ..... *C12Q 1/6886* (2013.01); *C12Q 2600/106* (2013.01); *C12Q 2600/156* (2013.01); *G01N 33/574* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,474,893 A | 10/1984 | Reading |
| 4,659,678 A | 4/1987 | Forrest et al. |
| 4,676,980 A | 6/1987 | Segel et al. |
| 4,727,022 A | 2/1988 | Skold et al. |
| 4,816,567 A | 3/1989 | Cabilly et al. |
| 5,018,067 A | 5/1991 | Mohlenbrock et al. |
| 5,194,392 A | 3/1993 | Geysen |
| 5,480,971 A | 1/1996 | Houghten et al. |
| 5,675,063 A | 10/1997 | Knight |
| 6,951,930 B2 | 10/2005 | Dempcy et al. |
| 2002/0038227 A1 | 3/2002 | Fey et al. |
| 2004/0122296 A1 | 6/2004 | Hatlestad et al. |
| 2004/0122297 A1 | 6/2004 | Stahmann et al. |

FOREIGN PATENT DOCUMENTS

| | | |
|---|---|---|
| EP | 0 394 827 A1 | 10/1990 |
| WO | WO /03016861 A2 | 2/2003 |

OTHER PUBLICATIONS

Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Hornakova et al. (Haematologica, vol. 96, No. 6, pp. 845-853, Mar. 10, 2011).*
Weigert et al. (J. Exp. Med. vol. 209, No. 2, pp. 259-273, Jan. 23, 2012).*
Marit et al. (PLOS, vol. 7, No. 8, pp. e43437, Aug. 16, 2012).*
Bhagwat et al. (Int. J. Hemato, vol. 97, pp. 695-702, 2013).*
Deshpande et al. (Leukemia, vol. 26, pp. 708-715, published on line Sep. 16, 2011).*
Deshpande et al. (Abstract 125, 2011 ASH Annual Meeting Abstracts, vol. 118, No. 21, Nov. 18, 2011).*
Mascarenhas et al. (Current Medicinal Chemistry, vol. 19, pp. 4399-4413, 2012) (Year: 2012).*
Levine et al. (Cancer Cell, vol. 7, pp. 387-396, Apr. 2005) (Year: 2005).*
Baxter et al. (The Lancet, vol. 365, pp. 1054-1061, Mar. 19, 2005) (Year: 2005).*
Hexner et al. Blood, vol. 111, No. 12, pp. 5663-5670, Jun. 2008 (Year: 2008).*
Ma et al. (Clinical Cancer Research, AACR International Conference: Molecular Diagnostics in Cacner Therapeutic Development, Sep. 22-25, 2008) (Year: 2008).*
Barovsky K., Nanotech. *Law & Bus.* 1(2): Article 14 (2004).
Chow et al., "Measurement of MAP Kinase Activation by Flow Cytometry Using Phospho-Specific Antibodies to MEK and ERK: Potential for Pharmacodynamic Monitoring of Signal Transduction Inhibitors", *Cytometry (Communications in Clinical Cytometry)*, 46: 72-78 (2001).
Cook, "Use and Misuse of the Receiver Operating Characteristic Curve in Risk Prediction", *Circulation* 2007, 115: 928-935.
Czernik et al. "Production of phosphorylation state-specific antibodies", *Methods In Enzymology*, 201:264-283 (1991).
Duplaa et al. "Quantitative analysis of polymerase chain reaction products using biotinylated dUTP incorporation", *Anal. Biochem.* 212(1), 229-236 (1993).
Fountoulakis et al., "Interferon {gamma} Receptor Extracellular Domain Expressed as IgG Fusion Protein in Chinese Hamster Ovary Cells: Purification, Biochemical Characterization, and Stoichiometry of Binding ", *J Biochem* 270: 3958-3964 (1995).
Gerber et al., "Absolute quantification of proteins and phosphoproteins from cell lysates by tandem MS", *Proc. Natl. Acad. Sci. U.S.A.* 100(12): 6940-5 (2003).
Huse W. et al., "Generation of a large combinatorial library of the immunoglobulin repertoire in phage lambda", *Science* 246:1275-81 (1989).
Kohler and Milstein, "Continuous cultures of fused cells secreting antibody of predefined specificity", *Nature*, 265:495-497 (1975).
Kohler and Milstein, "Derivation of specific antibody-producing tissue culture and tumor lines by cell fusion", *Eur. J. Immunol*, 6: 511-519 (1976).
Melby et al., "Quantitative measurement of human cytokine gene expression by polymerase chain reaction", *J. Immunol. Methods*, 159:235-244 (1993).
Merrifield, *J. Am. Chem. Soc.* 85: 2149-2154 (1963).

(Continued)

*Primary Examiner* — Jeanine A Goldberg
(74) *Attorney, Agent, or Firm* — Cooley LLP; Ivor R. Elrifi; Cynthia A. Kozakiewicz

(57) ABSTRACT

This present invention provides methods of treating of assessing/monitoring the responsiveness of a cancer cell to JAK inhibitor therapy.

11 Claims, 3 Drawing Sheets

Specification includes a Sequence Listing.

(56) References Cited

OTHER PUBLICATIONS

Morrison et al., "Chimeric human antibody molecules: mouse antigen-binding domains with human constant region domains", *Proc. Nat'l. Acad. Sci.* 81:6851-6855 (1984).

Mullinax et al., "Identification of human antibody fragment clones specific for tetanus toxoid in a bacteriophage lambda immunoexpression library", *Proc. Nat'l Acad. Sci.* 87: 8095-8099 (1990).

Neuberger et al., "Recombinant antibodies possessing novel effector functions", *Nature* 312:604-608 (1984).

O'Marcaigh AS and Jacobson RM, "Estimating the Predictive Value of a Diagnostic Test, How to Prevent Misleading or Confusing Results", *Clin. Ped.* 1993, 32(8): 485-491.

Pepe M.S. et al, "Limitations of the Odds Ratio in Gauging the Performance of a Diagnostic, Prognostic, or Screening Marker," *Am. J. Epidemiol*, 2004, 159 (9): 882-890.

Shultz, "Clinical Interpretation of Laboratory Procedures," chapter 14 in *Teitz, Fundamentals of Clinical Chemistry*, Burtis and Ashwood (eds.), 4th edition 1996, W.B. Saunders Company, pp. 192-199.

Spira G. et al., "The identification of monoclonal class switch variants by sib selection and an ELISA assay", *J. Immunol. Methods*, 74: 307-315 (1984).

Steplewski Z., et al., "Isolation and characterization of anti-monosialoganglioside monoclonal antibody 19-9 class-switch variants", *Proc. Nat'l. Acad. Sci.*, 82:8653-8657 (1985).

Traunecker et al., "Soluble CD4 molecules neutralize human immunodeficiency virus type 1", *Nature* 331: 84-86 (1988).

Zweig et al., "ROC Curve Analysis: An Example Showing The Relationships among Serum Lipid and Apolipoprotein Concentrations in Identifying Subjects with Coronory Artery Disease", *Clin. Chem.*, 1992, 38(8): 1425-1428.

Walker M. et al., "Interaction of human IgG chimeric antibodies with the human FcRI and FcRII receptors: requirements for antibody-mediated host cell-target cell interaction", *Molec. Immunol.* 26: 403-11 (1989).

Levine RL, Gilliland DG. Myeloproliferative disorders. *Blood* 2008; 112: 2190-2198.

James C, Ugo V, Le Couedic JP, Staerk J, Delhommeau F, Lacout C, et al. A unique clonal JAK2 mutation leading to constitutive signalling causes polycythaemia vera. *Nature* 2005; 434: 1144-1148.

Lucet IS, Fantino E, Styles M, Bamert R, Patel O, Broughton SE, et al. The structural basis of Janus kinase 2 inhibition by a potent and specific pan-Janus kinase inhibitor. *Blood* 2006; 107: 176-183.

Williams NK, Bamert RS, Patel O, Wang C, Walden PM, Wilks AF, et al. Dissecting specificity in the Janus kinases: the structures of JAK-specific inhibitors complexed to the JAK1 and JAK2 protein tyrosine kinase domains. *J Mol Biol* 2009; 387: 219-232.

Lu X, Levine R, Tong W, Wernig G, Pikman Y, Zarnegar S, et al. Expression of a homodimeric type I cytokine receptor is required for JAK2V617F-mediated transformation. *Proc Natl Acad Sci U S A* 2005; 102: 18962-18967.

Wernig G, Gonneville JR, Crowley BJ, Rodrigues MS, Reddy MM, Hudon HE, et al. The Jak2V617F oncogene associated with myeloproliferative diseases requires a functional FERM domain for transformation and for expression of the Myc and Pim proto-oncogenes. *Blood* 2008; 111: 3751-3759.

Verstovsek S, Kantarjian H, Mesa RA, Pardanani AD, Cortes-Franco J, Thomas DA, et al. Safety and efficacy of INCB018424, a JAK1 and JAK2 inhibitor, in myelofibrosis. *N Engl J Med* 2010; 363: 1117-1127.

Pardanani A, Gotlib JR, Jamieson C, Cortes JE, Talpaz M, Stone RM, et al. Safety and efficacy of TG101348, a selective JAK2 inhibitor, in myelofibrosis. *J Clin Oncol* 2011; 29: 789-796.

Tefferi A, Pardanani A. JAK inhibitors in myeloproliferative neoplasms: rationale, current data and perspective. *Blood Rev* 2011, 25: 229-237.

Hedvat M, Huszar D, Herrmann A, Gozgit JM, Schroeder A, Sheehy A, et al. The JAK2 inhibitor AZD1480 potently blocks Stat3 signaling and oncogenesis in solid tumors. *Cancer Cell* 2009; 16: 487-497.

Pardanani A, Lasho T, Smith G, Burns CJ, Fantino E, Tefferi A. CYT387, a selective JAK1/JAK2 inhibitor: in vitro assessment of kinase selectivity and preclinical studies using cell lines and primary cells from polycythemia vera patients. *Leukemia* 2009; 23: 1441-1445.

Quintas-Cardama A, Vaddi K, Liu P, Manshouri T, Li J, Scherle PA, et al. Preclinical characterization of the selective JAK1/2 inhibitor INCB018424: therapeutic implications for the treatment of myeloproliferative neoplasms. *Blood* 2010; 115: 3109-3117.

Tyner JW, Bumm TG, Deininger J, Wood L, Aichberger KJ, Loriaux MM, et al. CYT387, a novel JAK2 inhibitor, induces hematologic responses and normalizes inflammatory cytokines in murine myeloproliferative neoplasms. *Blood* 2010; 115: 5232-5240.

Wernig G, Kharas MG, Okabe R, Moore SA, Leeman DS, Cullen DE, et al. Efficacy of TG101348, a selective JAK2 inhibitor, in treatment of a murine model of JAK2V617F-induced polycythemia vera. *Cancer Cell* 2008; 13: 311-320.

George DJ, Dionne CA, Jani J, Angeles T, Murakata C, Lamb J, et al. Sustained in vivo regression of Dunning H rat prostate cancers treated with combinations of androgen ablation and Trk tyrosine inhibitors, CEP-751 (KT-6587) or CEP-701 (KT-5555). *Cancer Res* 1999; 59: 2395-2401.

Hexner EO, Serdikoff C, Jan M, Swider CR, Robinson C, Yang S, et al. Lestaurtinib (CEP701) is a JAK2 inhibitor that suppresses JAK2/STAT5 signaling and the proliferation of primary erythroid cells from patients with myeloproliferative disorders. *Blood* 2008; 111: 5663-5671.

Levis M, Allebach J, Tse KF, Zheng R, Baldwin BR, Smith BD, et al. A FLT3-targeted tyrosine kinase inhibitor is cytotoxic to leukemia cells in vitro and in vivo. *Blood* 2002; 99: 3885-3891.

Strock CJ, Park JI, Rosen M, Dionne C, Ruggeri B, Jones-Bolin S, et al. CEP-701 and CEP-751 inhibit constitutively activated RET tyrosine kinase activity and block medullary thyroid carcinoma cell growth. *Cancer Res* 2003; 63: 5559-5563.

Cools J, Stover EH, Boulton CL, Gotlib J, Legare RD, Amaral SM, et al. PKC412 overcomes resistance to imatinib in a murine model of FIP1L1-PDGFRalpha-induced myeloproliferative disease. *Cancer Cell* 2003; 3: 459-469.

Gorre ME, Mohammed M, Ellwood K, Hsu N, Paquette R, Rao PN, et al. Clinical resistance to STI-571 cancer therapy caused by BCR-ABL gene mutation or amplification. *Science* 2001; 293: 876-880.

Pao W, Miller VA, Politi KA, Riely GJ, Somwar R, Zakowski MF, et al. Acquired resistance of lung adenocarcinomas to gefitinib or erlotinib is associated with a second mutation in the EGFR kinase domain. *PLoS Med* 2005; 2: e73.

Schindler T, Bornmann W, Pellicena P, Miller WT, Clarkson B, Kuriyan J. Structural mechanism for STI-571 inhibition of abelson tyrosine kinase. *Science* 2000; 289: 1938-1942.

Tamborini E, Bonadiman L, Greco A, Albertini V, Negri T, Gronchi A, et al. A new mutation in the KIT ATP pocket causes acquired resistance to imatinib in a gastrointestinal stromal tumor patient. *Gastroenterology* 2004; 127: 294-299.

Bikadi Z, Hazai E. Application of the PM6 semi-empirical method to modeling proteins enhances docking accuracy of AutoDock. *J Cheminform* 2009; 1: 15.

Morris GM, Goodsell DS, Halliday RS, Huey R, Hart WE, Belew RK, et al. Automated docking using a Lamarckian genetic algorithm and an empirical binding free energy function. *J Comput Chem* 1998; 19: 1639-1662.

Walz C, Crowley BJ, Hudon HE, Gramlich JL, Neuberg DS, Podar K, et al. Activated Jak2 with the V617F point mutation promotes G1/S phase transition. *J Biol Chem* 2006; 281: 18177-18183.

Azam M, Latek RR, Daley GQ. Mechanisms of autoinhibition and STI-571/imatinib resistance revealed by mutagenesis of BCR-ABL. *Cell* 2003; 112: 831-843.

(56) References Cited

OTHER PUBLICATIONS

Ray A, Cowan-Jacob SW, Manley PW, Mestan J, Griffin JD. Identification of BCR-ABL point mutations conferring resistance to the Abl kinase inhibitor AMN107 (nilotinib) by a random mutagenesis study. *Blood* 2007; 109: 5011-5015.

Bercovich D, Ganmore I, Scott LM, Wainreb G, Birger Y, Elimelech A, et al. Mutations of JAK2 in acute lymphoblastic leukaemias associated with Down's syndrome. *Lancet* 2008; 372: 1484-1492.

Mullighan CG, Zhang J, Harvey RC, Collins-Underwood JR, Schulman BA, Phillips LA, et al. JAK mutations in high-risk childhood acute lymphoblastic leukemia. *Proc Natl Acad Sci U S A* 2009; 106: 9414-9418.

Reiter A, Walz C, Watmore A, Schoch C, Blau I, Schlegelberger B, et al. The t(8;9)(p22;p24) is a recurrent abnormality in chronic and acute leukemia that fuses PCM1 to JAK2. *Cancer Res* 2005; 65: 2662-2667.

Yoda A, Yoda Y, Chiaretti S, Bar-Natan M, Mani K, Rodig SJ, et al. Functional screening identifies CRLF2 in precursor B-cell acute lymphoblastic leukemia. *Proc Natl Acad Sci U S A* 2010; 107: 252-257.

Azam M, Seeliger MA, Gray NS, Kuriyan J, Daley GQ. Activation of tyrosine kinases by mutation of the gatekeeper threonine. *Nat Struct Mol Biol* 2008; 15: 1109-1118.

Zhao L, Dong H, Zhang CC, Kinch L, Osawa M, Iacovino M, et al. A JAK2 interdomain linker relays Epo receptor engagement signals to kinase activation. *J Biol Chem* 2009; 284: 26988-26998.

Hornakova T, Springuel L, Devreux J, Dusa A, Constantinescu SN, Knoops L, et al. Oncogenic JAK1 and JAK2-activating mutations resistant to ATP-competitive inhibitors. *Haematologica* 2011; 96: 845-853.

Koptyra M, Cramer K, Slupianek A, Richardson C, Skorski T. BCR/ABL promotes accumulation of chromosomal aberrations induced by oxidative and genotoxic stress. *Leukemia* 2008; 22: 1969-1972.

Sattler M, Verma S, Shrikhande G, Byrne CH, Pride YB, Winkler T, et al. The BCR/ABL tyrosine kinase induces production of reactive oxygen species in hematopoietic cells. *J Biol Chem* 2000; 275: 24273-24278.

Reddy MM, Fernandes MS, Salgia R, Levine RL, Griffin JD, Sattler M. NADPH oxidases regulate cell growth and migration in myeloid cells transformed by oncogenic tyrosine kinases. *Leukemia* 2011; 25: 281-289.

Marubayashi S, Koppikar P, Taldone T, Abdel-Wahab O, West N, Bhagwat N, et al. HSP90 is a therapeutic target in JAK2-dependent myeloproliferative neoplasms in mice and humans. *J Clin Invest* 2010; 120: 3578-3593.

Swords R, Kelly K, Carew J, Nawrocki S, Mahalingam D, Sarantopoulos J, et al. The Pim Kinases: New Targets for Drug Development. *Curr Drug Targets* 2011, 12, 2059-2066.

Reddy MM, Deshpande A., Sattler M. Targeting JAK2 in the therapy of myeloproliferative neoplasms. *Expert Opinion Ther Targets* 2012, 16(3), 313-324.

* cited by examiner

METHODS OF PREDICTING RESISTANCE TO JAK INHIBITOR THERAPY

RELATED APPLICATIONS

This application claims benefit to and priority of U.S. Application No. 61/658,711, filed on Jun. 12, 2012, the contents of which are incorporated herein in their entirety.

INCORPORATION BY REFERENCE OF SEQUENCE LISTING

The contents of the text file named "20363-066001US_ST25.txt", which was created on Sep. 15, 2013 and is 65 KB in size, are hereby incorporated by reference in their entirety.

GOVERNMENT INTEREST

This invention was made with government support under R01 CA140545 and RC2 CA148268 awarded by the National Cancer Institute and the National Institutes of Health. The United States government has certain rights in the invention.

FIELD OF THE INVENTION

The invention relates to generally to the predicting a subjects response to JAK inhibitor therapy.

BACKGROUND OF THE INVENTION

Myeloproliferative neoplasms (MPNs) are frequently associated with a mutation in the non-receptor tyrosine kinase JAK2 at codon 617 that changes valine (V) to phenylalanine (F). This activating JAK2V617F mutation is not only found in the majority of patients with myeloproliferative neoplasms, including polycythemia vera, essential thrombocythemia, and idiopathic myelofibrosis, but can also be present at lower frequency in other myeloid malignancies, including acute myeloid leukemia and myelodysplastic syndromes. JAK2V617F is thought to be instrumental for the overproduction of myeloid lineage cells and in mice—it is sufficient by itself to cause a myeloproliferative disease. Even though the crystal structure of the JAK2 kinase domain has been solved, it is not known how exactly the V617F mutation in the pseudokinase domain leads to constitutive activation. The JAK2V617F mutation seems insufficient for its kinase activation and association with a cytokine receptor, such as the erythropoietin receptor (EpoR), appears to be required. Lack of a functional FERM domain in JAK2V617F, which mediates interaction with cytokine receptors, results in a loss of its transforming activity. It is likely that inhibitory constraints, normally overcome by ligand binding, are targeted by the JAK2V617F mutation, therefore leading to hyperresponsiveness or factor-independent growth.

Most, if not all, tyrosine kinase inhibitors that are currently used to target transforming tyrosine kinase oncogenes in various cancers are susceptible to resistance, as a result of point mutations in the corresponding kinase domain. Thus, a need exists to identify mutations in the JAK2 JH1 domain that would confer resistance and compare the sensitivity of different JAK inhibitors that are currently in clinical trials towards these mutations.

SUMMARY OF THE INVENTION

The invention is based upon the discovery of biomarkers associated with the responsiveness to JAK inhibitor therapy.

In one aspect the invention provides a method of assessing the effectiveness of a JAK inhibitor treatment regimen of a subject having a myeloproliferative malignacy with the JAK2V617F mutation by obtaining a sample from the subject and detecting the presence or absence of one or more point mutations. The mutations are Y931C, G935R, R938L, I960V, and E985K in the kinase domain of the JAK2V617F polypeptide. The mutation indicates the subject is resistant to JAK inhibitor treatment.

In another aspect, the invention provides a method of selecting a treatment regimen for a subject having a myeloproliferative malignancy with the JAK2V617F mutation by obtaining a sample from the subject and detecting the presence or absence of one or more point mutations. The mutations are Y931C, G935R, R938L, I960V, and E985K in the kinase domain of the JAK2V617F polypeptide. The absence of the mutation indicates the subject should receive JAK inhibitor treatment. The presence of the mutation indicates the subject should not receive JAK inhibitor treatment.

The JAK inhibitor is an ATP-competitive inhibitor. Exemplary JAK inhibitors include, but are not limited to, ruxolitinib, CYT-387, TG101348, AZD1480, lestaurtinib, tofacitinib, pacritinib, baricitinib, BMS-911543, LY2784544, XL019, and NS018.

The myeloproliferative malignacy is polycythemia vera, essential thrombocythemia, idiopathic myelofibrosis, acute myeloid leukemia or myelodysplastic syndrome.

Also included in the invention is a kit for the detection of mutant JAK2V617F nucleic acid or polypeptide in a biological sample. The kit contains a reagent that detects a mutation including Y931C, G935R, R938L, I960V, and/or E985K in the JAK2 kinase domain and one or more secondary reagents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

Mutated amino acids are depicted in the panels on the right. (C) Surface electrostatic potential representation of the native (left) and G935R mutant (right) containing JAK2 JH1 domain with ruxolitinib. Charged surfaces are displayed: positive (black), negative (grey), and non-polar (white).

Figure 2:
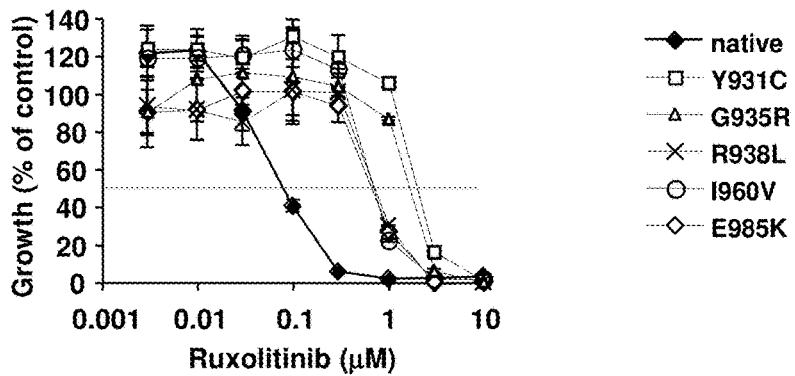
Figure 2:
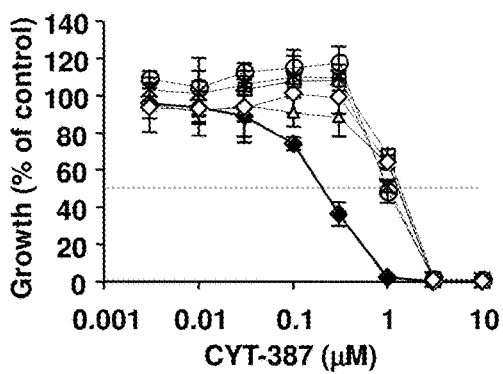
Figure 2:
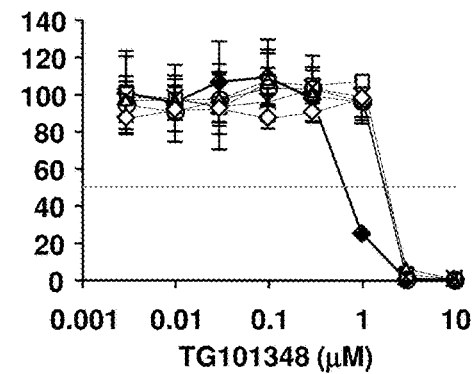
Figure 2:
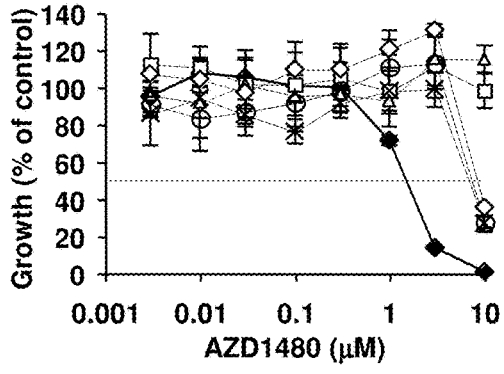
Figure 2:
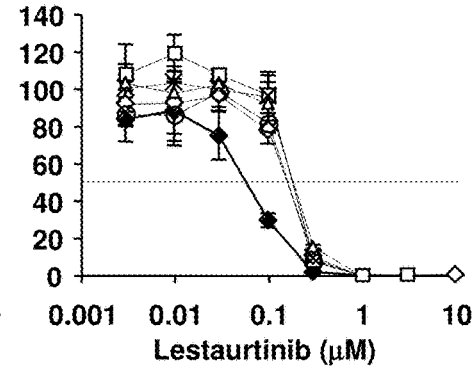

FIG. 2 is a panel of five graphs demonstrating that the identified mutations confer resistance to JAK2 tyrosine kinase inhibitors. Growth of BaF3.EpoR cells expressing JAK2V617F (♦) and the additional Y931C (□), G935R (Δ), R938L (X), I960V (○) or E985K (◊) mutations was determined in response to (A) ruxolitinib; (B) CYT-387; (C) TG101348; (D) AZD1480; and (E) lestaurtinib at various concentrations, as indicated (n=4). Changes in growth in response to JAK2 inhibitors were calculated relative to cells that were treated with the solvent DMSO.

Figure 3:
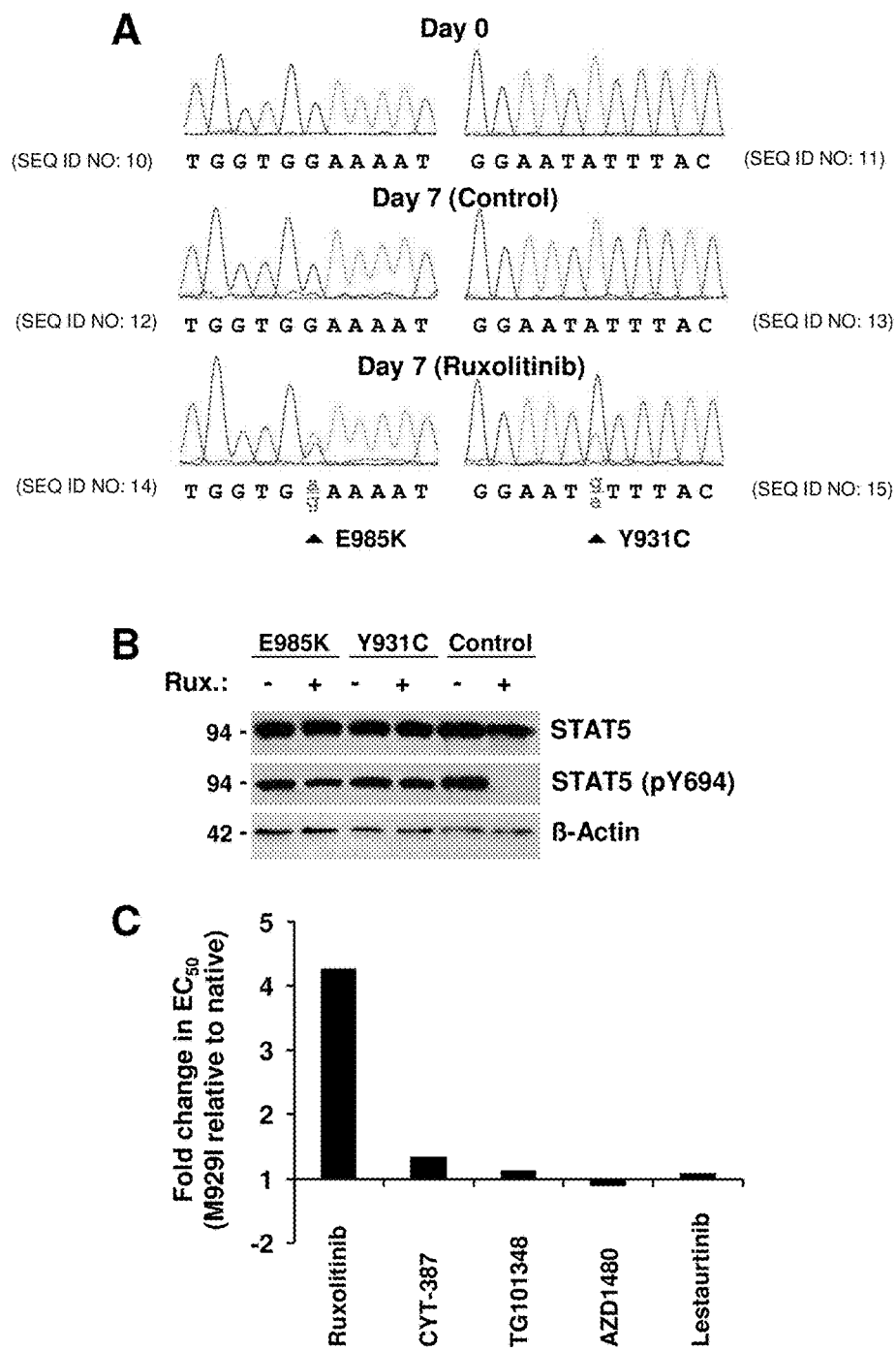

FIG. 3 shows the characterization of ruxolitinib resistant JAK2V617F mutations. (A) Genomic DNAs from a polyclonal population of BaF3.EpoR. JAK2V617F cells, containing 1% of JAK2V617F mutant expressing cells were analyzed at day 0 and day 7 after treatment with either DMSO (control) or ruxolitinib (300 nM) for the presence of E985K and Y931C substitution (arrows indicate position of corresponding base substitution). Partial chromatograms of the forward strand are shown. (B) Expression of STAT5, phospho-Y694 STAT5 and β-actin was determined by immunoblotting in BaF3.EpoR cells expressing JAK2V617F (control) and cells containing the additional E985K or Y931C mutation. Cells were either treated with DMSO or 300 nM ruxolitinib. (C) Relative changes in the half maximal effective concentration (EC50) values were determined in response to ruxolitinib for BaF3.EpoR.JAK2V617F.M929I cells, relative to cells expressing native JAK2V617F.

DETAILED DESCRIPTION OF THE INVENTION

The present invention relates to the identification of biomarkers associated with the responsiveness to JAK inhibitor therapy. Specifically, the biomarkers are non-synonymous point mutations in the JAK2V617F gene leading to an amino acid substitution at various positions in the JAK2 JH1 domain of the JAK2V617F polypeptide. In particular, these mutations result in a tyrosine to cysteine at position 931 (Y931C); a glycine to arginine at position 935 (G935R); an arginine to leucine at position 938 (R938L); an isoleucine to valine at position 960 (I960V), and a glutamic acid to a lysine at position 985 (E985K).

The mRNA sequence of JAK2 with the V617F mutation corresponds to GenBank: AY973034.1.

```
                                                              (SEQ ID NO: 1)
   1 tttctcttct gcagaaaaag aggctcttcc tcctcctccc gcgacggcaa atgttctgaa 61 aaagactctg catgggaatg gcctgcctta cgatgacaga aatggaggga acatccacct 121 cttctatata tcagaatggt gatatttctg gaaatgccaa ttctatgaag caaatagatc 181 cagttcttca ggtgtatctt taccattccc ttgggaaatc tgaggcagat tatctgacct 241 ttccatctgg ggagtatgtt gcagaagaaa tctgtattgc tgcttctaaa gcttgtggta 301 tcacacctgt gtatcataat atgtttgctt taatgagtga aacagaaagg atctggtatc 361 cacccaacca tgtcttccat atagatgagt caaccaggca taatgtactc tacagaataa 421 gattttactt tcctcgttgg tattgcagtg gcagcaacag agcctatcgg catggaatat 481 ctcgaggtgc tgaagctcct cttcttgatg actttgtcat gtcttacctc tttgctcagt 541 ggcggcatga ttttgtgcac ggatggataa aagtacctgt gactcatgaa acacaggaag 601 aatgtcttgg gatggcagtg ttagatatga tgagaatagc caaagaaaac gatcaaaccc 661 cactggccat ctataactct atcagctaca agacattctt accaaaatgt attcgagcaa 721 agatccaaga ctatcatatt ttgacaagga agcgaataag gtacagattt cgcagattta 781 ttcagcaatt cagccaatgc aaagccactg ccagaaactt gaaacttaag tatcttataa 841 atctggaaac tctgcagtct gccttctaca cagagaaatt tgaagtaaaa gaacctggaa 901 gtggtccttc aggtgaggag atttttgcaa ccattataat aactggaaac ggtggaattc 961 agtggtcaag agggaaacat aaagaaagtg agacactgac agaacaggat ttacagttat 1021 attgcgattt tcctaatatt attgatgtca gtattaagca agcaaaccaa gagggttcaa 1081 atgaaagccg agttgtaact atccataagc aagatggtaa aaatctggaa attgaactta 1141 gctcattaag ggaagctttg tctttcgtgt cattaattga tggatattat agattaactg 1201 cagatgcaca tcattacctc tgtaaagaag tagcacctcc agccgtgctt gaaaatatac 1261 aaagcaactg tcatggccca atttcgatgg attttgccat tagtaaactg aagaaagcag 1321 gtaatcagac tggactgtat gtacttcgat gcagtcctaa ggactttaat aaatattttt 1381 tgactttgc tgtcgagcga gaaaatgtca ttgaatataa acactgtttg attacaaaaa
```

-continued

```
1441 atgagaatga agagtacaac ctcagtggga caaagaagaa cttcagcagt cttaaagatc
1501 ttttgaattg ttaccagatg gaaactgttc gctcagacaa tataattttc cagtttacta
1561 aatgctgtcc cccaaagcca aaagataaat caaaccttct agtcttcaga acgaatggtg
1621 tttctgatgt accaacctca ccaacattac agaggcctac tcatatgaac caaatggtgt
1681 ttcacaaaat cagaaatgaa gatttgatat ttaatgaaag ccttggccaa ggcacttttta
1741 caaagatttt taaaggcgta cgaagagaag taggagacta cggtcaactg catgaaacag
1801 aagttctttt aaaagttctg gataaagcac acagaaacta ttcagagtct ttctttgaag
1861 cagcaagtat gatgagcaag ctttctcaca agcatttggt tttaaattat ggagtatgtt
1921 tctgtggaga cgagaatatt ctggttcagg agtttgtaaa atttggatca ctagatacat
1981 atctgaaaaa gaataaaaat tgtataaata tattatggaa acttgaagtt gctaaacagt
2041 tggcatgggc catgcatttt ctagaagaaa acacccttat tcatgggaat gtatgtgcca
2101 aaaatattct gcttatcaga gaagaagaca ggaagacagg aaatcctcct ttcatcaaac
2161 ttagtgatcc tggcattagt attacagttt tgccaaagga cattcttcag gagagaatac
2221 catgggtacc acctgaatgc attgaaaatc ctaaaaattt aaatttggca acagacaaat
2281 ggagttttgg taccactttg tgggaaatct gcagtggagg agataaacct ctaagtgctc
2341 tggattctca aagaaagcta caattttatg aagataggca tcagcttcct gcaccaaagt
2401 gggcagaatt agcaaacctt ataaataatt gtatggatta tgaaccagat ttcaggcctt
2461 ctttcagagc catcatacga gatcttaaca gtttgtttac tccagattat gaactattaa
2521 cagaaaatga catgttacca aatatgagga taggtgccct ggggttttct ggtgcctttg
2581 aagaccggga tcctacacag tttgaagaga gacatttgaa atttctacag caacttggca
2641 agggtaattt tgggagtgtg gagatgtgcc ggtatgaccc tctacaggac aacactgggg
2701 aggtggtcgc tgtaaaaaag cttcagcata gtactgaaga gcacctaaga gactttgaaa
2761 gggaaattga atcctgaaa tccctacagc atgacaacat tgtaaagtac aagggagtgt
2821 gctacagtgc tggtcggcgt aatctaaaat taattatgga atatttacca tatggaagtt
2881 tacgagacta tcttcaaaaa cataaagaac ggatagatca cataaaactt ctgcagtaca
2941 catctcagat atgcaagggt atggagtatc ttggtacaaa aaggtatatc cacagggatc
3001 tggcaacgag aaatatattg gtggagaacg agaacagagt taaaattgga gattttgggt
3061 taaccaaagt cttgccacaa gacaaagaat actataaagt aaaagaacct ggtgaaagtc
3121 ccatattctg gtatgctcca gaatcactga cagagagcaa gttttctgtg gcctcagatg
3181 tttggagctt gggagtggtt ctgtatgaac ttttcacata cattgagaag agtaaaagtc
3241 caccagcgga atttatgcgt atgattggca atgacaaaca aggacagatg atcgtgttcc
3301 atttgataga acttttgaag aataatggaa gattaccaag accagatgga tgcccagatg
3361 agatctatat gatcatgaca gaatgctgga acaataatgt aaatcaacgc ccctcctta
3421 gggatctagc tcttcgagtg gatcaaataa gggataacat ggctggatga agaaatgac
3481 cttcattctg agaccaaagt agatttacag aacaaagttt tatatttcac attgctgtgg
3541 actattatta catatatcat tattatataa atcatgatgc tagccagcaa agatgtgaaa
3601 atatctgctc aaaactttca aagtttagta agttttttctt catgaggcca cc
```

The amino acid sequence of JAK2 with the V617F mutation corresponds to GenBank: AAY22962.1.

```
                                                           (SEQ ID NO: 2)
   1 mgmacltmte megtstssiy qngdisgnan smkqidpvlq vylyhslgks eadyltfpsg 61 eyvaeeicia askacgitpv yhnmfalmse teriwyppnh vfhidestrh nvlyrirfyf 121 prwycsgsnr ayrhgisrga eapllddfvm sylfaqwrhd fvhgwikvpv thetqeeclg 181 mavldmmria kendqtplai ynsisyktfl pkcirakiqd yhiltrkrir yrfrrfiqqf 241 sqckatarnl klkylinlet lqsafytekf evkepgsgps geeifatiii tgnggiqwsr 301 gkhkesetlt eqdlqlycdf pniidvsikq anqegsnesr vvtihkqdgk nleielsslr 361 ealsfvslid gyyrltadah hylckevapp avleniqsnc hgpismdfai sklkkagnqt 421 glyvlrcspk dfnkyfltfa verenvieyk hclitknene eynlsgtkkn fsslkdllnc 481 yqmetvrsdn iifqftkccp pkpkdksnll vfrtngvsdv ptsptlqrpt hmnqmvfhki 541 rnedlifnes lgqgtftkif kgvrrevgdy gqlhetevll kvldkahrny sesffeaasm 601 msklshkhlv lnygvcfcgd enilvqefvk fgsldtylkk nkncinilwk levakqlawa 661 mhfleentli hgnvcaknil lireedrktg nppfiklsdp gisitvlpkd ilqeripwvp 721 pecienpknl nlatdkwsfg ttlweicsgg dkplsaldsq rklqfyedrh qlpapkwael 781 anlinncmdy epdfrpsfra iirdlnslft pdyelltend mlpnmrigal gfsgafedrd 841 ptqfeerhlk flqqlgkgnf gsvemcrydp lqdntgevva vkklqhstee hlrdfereie 901 ilkslqhdni vkykgvcysa grrnlklime ylpygslrdy lqkhkeridh ikllqytsqi 961 ckgmeylgtk ryihrdlatr nilvenenrv kigdfgltkv lpqdkeyykv kepgespifw 1021 yapesltesk fsvasdvwsf gvvlyelfty ieksksppae fmrmigndkq gqmivfhlie 1081 llknngrlpr pdgcpdeiym imtecwnnnv nqrpsfrdla lrvdqirdnm ag
```

JAK inhibitors suitable for human administration are known in the art and include for example, ruxolitinib (INCB018424), CYT-387, TG101348 (SAR302503), AZD1480, lestaurtinib (CEP-701), tofacitinib (CP-690, 550), pacritinib (SB1518), baricitinib (LY3009104, INCB28050), BMS-911543, LY2784544, XL019, and NS018.

Ruxolitinib (Jakafi™, INCB018424) is a potent, orally available, selective inhibitor of both JAK1 and JAK2 of the JAK-STAT signaling pathway. Ruxolitinib was initially developed to target the constitutive activation of the JAK-STAT pathway in patients with myeloproliferative neoplasms (MPNs).

CYT387 is an inhibitor of Janus kinases JAK1 and JAK2, acting as an ATP competitor with IC50 values of 11 and 18 nM, respectively. The inhibitor is significantly less active towards other kinases, including JAK3 (IC50=0.16 µM).

TG101348 (SAR302503) is an orally available inhibitor of Janus kinase 2 (JAK-2) developed for the treatment of patients with myeloproliferative diseases including myelofibrosis. TG101348 acts as a competitive inhibitor of protein kinase JAK-2 with IC50=6 nM; related kinases FLT3 and RET are also sensitive, with IC50=25 nM and IC50=17 nM, respectively. Significantly less activity was observed against other tyrosine kinases including JAK3 (IC50=169 nM). In treated cells, the inhibitor blocks downstream cellular signaling (JAK-STAT) leading to suppression of proliferation and induction of apoptosis.

AZD1480 is an orally bioavailable inhibitor of Janus-associated kinase 2 (JAK2) with potential antineoplastic activity. JAK2 inhibitor AZD 1480 inhibits JAK2 activation, leading to the inhibition of the JAK/STAT (signal transducer and activator of transcription) signaling including activation of STAT3.

Lestaurtinib (CEP-701) is a tyrosine kinase inhibitor structurally related to staurosporine.

Figure 1:
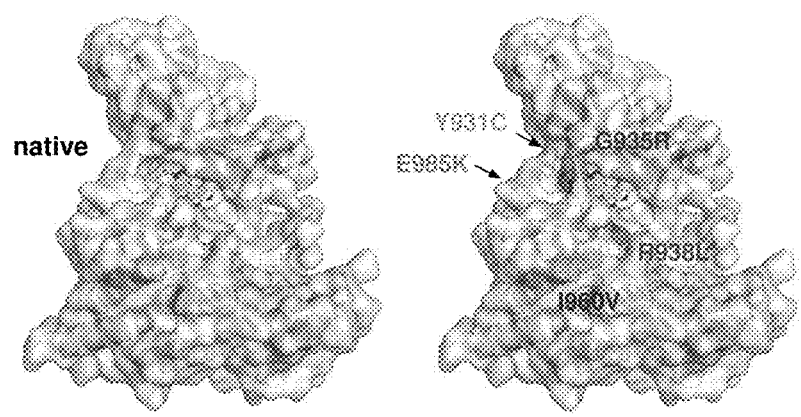
FIG. 1 is a series of cartoon representations depicting the structural analysis of JAK2V617F kinase domain mutations. (A) Cartoon representation of ruxolitinib-docked JAK2 kinase domain (left) and JAK2 with location of point mutations, as indicated, that lead to drug resistance (right). Ruxolitinib molecule is represented in stick representation in the binding site (left and right). The I960V sidechain is buried within the protein interior (dotted line). (B) Enlarged representation of ruxolitinib binding pocket with secondary structure elements (cartoon) and the interactions of the sidechains (labeled sticks) with the inhibitor. Hydrogen-bonds between the inhibitor and the protein are indicated as dotted lines (one hydrogen-bond between backbone of Y931 and L932; and two hydrogen-bonds with R980 and N981 and pyrrolopyrimidine ring of the inhibitor; additional hydrogen bonds are with water molecules (spheres)).
Figure 1:
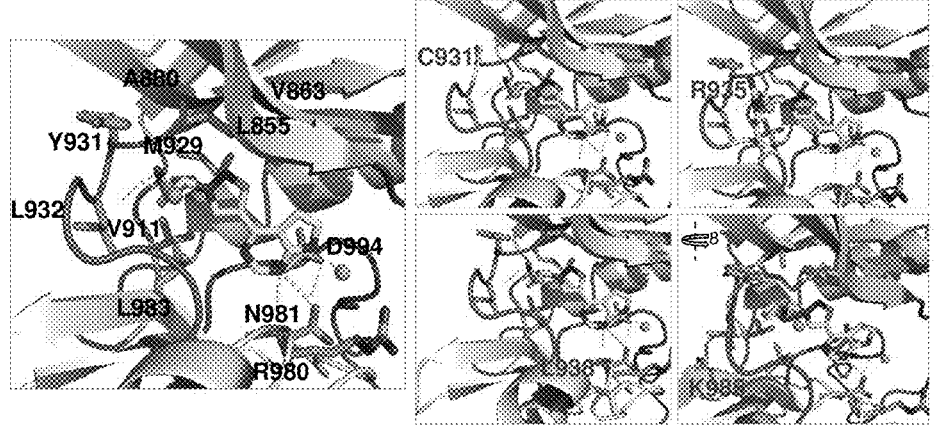
Figure 1:
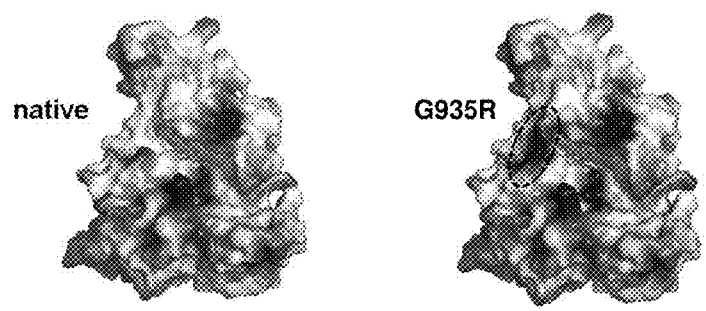

Tofacitinib (Xeljanz®, tascotinib, or CP-690,550) is a known inhibitor of JAK1 and JAK3. Data described herein demonstrate that tofacitinib also binds to the ATP-binding pocket of JAK2 (FIG. 1A). Tofacitinib is used to inhibit JAK-STAT signaling, and is used for treatment of rheumatoid arthritis.

Pacritinib (SB1815) is an orally bioavailable inhibitor of JAK2 and the JAK2 mutant JAK2V617F with potential antineoplastic activity. Pacritinib competes with JAK2 for ATP binding, which may result in inhibition of JAK2 activation, inhibition of the JAK-STAT signaling pathway, and therefore caspase-dependent apoptosis. Pacritinib is currently investigated for its utility in treatment of myeloproliferative disorders.

Baricitinib (LY3009104, INCB28050) is an orally bioavailable inhibitor of JAK1 and JAK2 with IC50=5.9 nm and IC50=5.7, nm respectively. Baricitinib preferentially inhibits JAK1 and JAK2, with 10-fold selectivity over Tyk2 and 100-fold over JAK3. The drug has shown efficacy in treatment of rheumatoid arthritis.

BMS-911543 a potent and selective small-molecule inhibitor of the Janus kinase (JAK) family member, JAK2 that has shown anti-proliferative activity in patients with JAK2V617F positive myeloproliferative neoplasms.

LY2784544 has been identified as a highly selective small molecule inhibitor of JAK2-V617F, and has been investigated for treatment efficacy in patients with myeloproliferative neoplasms.

XL019 is an orally bioavailable inhibitor of Janus-associated kinase 2 (JAK2) with potential antineoplastic activity. XL019 inhibits the activation of JAK2 as well as the mutated form JAK2V617F, which may result in the inhibition of the JAK-STAT signaling pathway and may induce apoptosis.

NS018 is a potent JAK2 inhibitor with some inhibition of Src-family kinases. NS018 has been shown to be highly active against JAK2 with a 50% inhibition (IC50) of <1 nM, and had 30-50-fold greater selectivity for JAK2 over other JAK-family kinases.

While JAK inhibitor therapy alone or in combination has shown a clinical benefit in treating myeloproliferative neoplasms (MPNs), a need exists for the identification of biomarkers that are predictive of responsiveness to JAK inhibitor therapy.

Accordingly, the invention provides methods of determining the responsiveness, e.g., sensitivity or resistance, of a cancer cell to JAK inhibitor therapy. These methods are also useful for monitoring subjects undergoing treatments and therapies for cancer, such as for example, myeloproliferative neoplasms, and for selecting therapies and treatments that would be efficacious in subjects having cancer, wherein selection and use of such treatments and therapies slow the progression of cancer. More specifically, the invention provides methods of determining whether a patient with a myeloproliferative neoplasm will be responsive to JAK inhibitor therapy.

Five different non-synonymous point mutations in the JH1 domain of the JAK2 tyrosine kinase that confer JAK inhibitor resistance are described herein. These mutations result in a tyrosine to cysteine at position 931 (Y931C); a glycine to arginine at position 935 (G935R); an arginine to leucine at position 938 (R938L); an isoleucine to valine at position 960 (I960V), and a glutamic acid to a lysine at position 985 (E985K).

The amino acid sequence for JAK2V617F with Y931C mutation is as follows:

(SEQ ID NO: 16)
```
   1 mgmacltmte megtstssiy qngdisgnan smkqidpvlq vylyhslgks eadyltfpsg
  61 eyvaeeicia askacgitpv yhnmfalmse teriwyppnh vfhidestrh nvlyrirfyf
 121 prwycsgsnr ayrhgisrga eapllddfvm sylfaqwrhd fvhgwikvpv thetqeeclg
 181 mavldmmria kendqtplai ynsisyktfl pkcirakiqd yhiltrkrir yrfrrfiqqf
 241 sqckatarnl klkylinlet lqsafytekf evkepgsgps geeifatiii tgnggiqwsr
 301 gkhkesetlt eqdlqlycdf pniidvsikq anqegsnesr vvtihkqdgk nleielsslr
 361 ealsfvslid gyyrltadah hylckevapp avleniqsnc hgpismdfai sklkkagnqt
 421 glyvlrcspk dfnkyfltfa verenvieyk hclitknene eynlsgtkkn fsslkdllnc
 481 yqmetvrsdn iifqftkccp pkpkdksnll vfrtngvsdv ptsptlqrpt hmnqmvfhki
 541 rnedlifnes lgqgtftkif kgvrrevgdy gqlhetevll kvldkahrny sesffeaasm
 601 msklshkhlv lnygvcfcgd enilvqefvk fgsldtylkk nkncinilwk levakqlawa
 661 mhfleentli hgnvcaknil lireedrktg nppfiklsdp gisitvlpkd ilqeripwvp
 721 pecienpknl nlatdkwsfg ttlweicsgg dkplsaldsq rklqfyedrh qlpapkwael
 781 anlinncmdy epdfrpsfra iirdlnslft pdyelltend mlpnmrigal gfsgafedrd
 841 ptqfeerhlk flqqlgkgnf gsvemcrydp lqdntgevva vkklqhstee hlrdfereie
 901 ilkslqhdni vkykgvcysa grrnlklime clpygslrdy lqkhkeridh ikllqytsqi
 961 ckgmeylgtk ryihrdlatr nilvenenrv kigdfgltkv lpqdkeyykv kepgespifw
1021 yapesltesk fsvasdvwsf gvvlyelfty ieksksppae fmrmigndkq gqmivfhlie
1081 llknngrlpr pdgcpdeiym imtecwnnnv nqrpsfrdla lrvdqirdnm ag
```

The amino acid sequence for JAK2V617F with G935R mutation is as follows:

(SEQ ID NO: 17)
```
   1 mgmacltmte megtstssiy qngdisgnan smkqidpvlq vylyhslgks eadyltfpsg
  61 eyvaeeicia askacgitpv yhnmfalmse teriwyppnh vfhidestrh nvlyrirfyf
 121 prwycsgsnr ayrhgisrga eapllddfvm sylfaqwrhd fvhgwikvpv thetqeeclg
 181 mavldmmria kendqtplai ynsisyktfl pkcirakiqd yhiltrkrir yrfrrfiqqf
 241 sqckatarnl klkylinlet lqsafytekf evkepgsgps geeifatiii tgnggiqwsr
 301 gkhkesetlt eqdlqlycdf pniidvsikq anqegsnesr vvtihkqdgk nleielsslr
```

-continued

```
 361 ealsfvslid gyyrltadah hylckevapp avleniqsnc hgpismdfai sklkkagnqt 421 glyvlrcspk dfnkyfltfa verenvieyk hclitknene eynlsgtkkn fsslkdllnc 481 yqmetvrsdn iifqftkccp pkpkdksnll vfrtngvsdv ptsptlqrpt hmnqmvfhki 541 rnedlifnes lgqgtftkif kgvrrevgdy gqlhetevll kvldkahrny sesffeaasm 601 msklshkhlv lnygvcfcgd enilvqefvk fgsldtylkk nkncinilwk levakqlawa 661 mhfleentli hgnvcaknil lireedrktg nppfiklsdp gisitvlpkd ilqeripwvp 721 pecienpknl nlatdkwsfg ttlweicsgg dkplsaldsq rklqfyedrh qlpapkwael 781 anlinncmdy epdfrpsfra iirdlnslft pdyelltend mlpnmrigal gfsgafedrd 841 ptqfeerhlk flqqlgkgnf gsvemcrydp lqdntgevva vkklqhstee hlrdfereie 901 ilkslqhdni vkykgvcysa grrnlklime ylpyrslrdy lqkhkeridh ikllqytsqi 961 ckgmeylgtk ryihrdlatr nilvenenrv kigdfgltkv lpqdkeyykv kepgespifw 1021 yapesltesk fsvasdvwsf gvvlyelfty iekskspppae fmrmigndkq gqmivfhlie 1081 llknngrlpr pdgcpdeiym imtecwnnnv nqrpsfrdla lrvdqirdnm ag
```

The amino acid sequence for JAK2V617F with R938L mutation is as follows:

(SEQ ID NO: 18)
```
   1 mgmacltmte megtstssiy qngdisgnan smkqidpvlq vylyhslgks eadyltfpsg 61 eyvaeeicia askacgitpv yhnmfalmse teriwyppnh vfhidestrh nvlyrirfyf 121 prwycsgsnr ayrhgisrga eaplldddfvm sylfaqwrhd fvhgwikvpv thetqeeclg 181 mavldmmria kendqtplai ynsisyktfl pkcirakiqd yhiltrkrir yrfrrfiqqf 241 sqckatarnl klkylinlet lqsafytekf evkepgsgps geeifatiii tgnggiqwsr 301 gkhkesetlt eqdlqlycdf pniidvsikq anqegsnesr vvtihkqdgk nleielsslr 361 ealsfvslid gyyrltadah hylckevapp avleniqsnc hgpismdfai sklkkagnqt 421 glyvlrcspk dfnkyfltfa verenvieyk hclitknene eynlsgtkkn fsslkdllnc 481 yqmetvrsdn iifqftkccp pkpkdksnll vfrtngvsdv ptsptlqrpt hmnqmvfhki 541 rnedlifnes lgqgtftkif kgvrrevgdy gqlhetevll kvldkahrny sesffeaasm 601 msklshkhlv lnygvcfcgd enilvqefvk fgsldtylkk nkncinilwk levakqlawa 661 mhfleentli hgnvcaknil lireedrktg nppfiklsdp gisitvlpkd ilqeripwvp 721 pecienpknl nlatdkwsfg ttlweicsgg dkplsaldsq rklqfyedrh qlpapkwael 781 anlinncmdy epdfrpsfra iirdlnslft pdyelltend mlpnmrigal gfsgafedrd 841 ptqfeerhlk flqqlgkgnf gsvemcrydp lqdntgevva vkklqhstee hlrdfereie 901 ilkslqhdni vkykgvcysa grrnlklime ylpygslldy lqkhkeridh ikllqytsqi 961 ckgmeylgtk ryihrdlatr nilvenenrv kigdfgltkv lpqdkeyykv kepgespifw 1021 yapesltesk fsvasdvwsf gvvlyelfty iekskspppae fmrmigndkq gqmivfhlie 1081 llknngrlpr pdgcpdeiym imtecwnnnv nqrpsfrdla lrvdqirdnm ag
```

The amino acid sequence for JAK2V617F with I960V mutation is as follows:

(SEQ ID NO: 19)
```
   1 mgmacltmte megtstssiy qngdisgnan smkqidpvlq vylyhslgks eadyltfpsg 61 eyvaeeicia askacgitpv yhnmfalmse teriwyppnh vfhidestrh nvlyrirfyf
```

-continued

```
121 prwycsgsnr ayrhgisrga eapllddfvm sylfaqwrhd fvhgwikvpv thetqeeclg 181 mavldmmria kendqtplai ynsisyktfl pkcirakiqd yhiltrkrir yrfrrfiqqf 241 sqckatarnl klkylinlet lqsafytekf evkepgsgps geeifatiii tgnggiqwsr 301 gkhkesetlt eqdlqlycdf pniidvsikq anqegsnesr vvtihkqdgk nleielsslr 361 ealsfvslid gyyrltadah hylckevapp avleniqsnc hgpismdfai sklkkagnqt 421 glyvlrcspk dfnkyfltfa verenvieyk hclitknene eynlsgtkkn fsslkdllnc 481 yqmetvrsdn iifqftkccp pkpkdksnll vfrtngvsdv ptsptlqrpt hmnqmvfhki 541 rnedlifnes lgqgtftkif kgvrrevgdy gqlhetevll kvldkahrny sesffeaasm 601 msklshkhlv lnygvcfcgd enilvqefvk fgsldtylkk nkncinilwk levakqlawa 661 mhfleentli hgnvcaknil lireedrktg nppfiklsdp gisitvlpkd ilqeripwvp 721 pecienpknl nlatdkwsfg ttlweicsgg dkplsaldsq rklqfyedrh qlpapkwael 781 anlinncmdy epdfrpsfra iirdlnslft pdyelltend mlpnmrigal gfsgafedrd 841 ptqfeerhlk flqqlgkgnf gsvemcrydp lqdntgevva vkklqhstee hlrdfereie 901 ilkslqhdni vkykgvcysa grrnlklime ylpygslrdy lqkhkeridh ikllqytsqv 961 ckgmeylgtk ryihrdlatr nilvenenrv kigdfgltkv lpqdkeyykv kepgespifw 1021 yapesltesk fsvasdvwsf gvvlyelfty iekskspppae fmrmigndkq gqmivfhlie 1081 llknngrlpr pdgcpdeiym imtecwnnnv nqrpsfrdla lrvdqirdnm ag
```

The amino acid sequence for JAK2V617F with E985K[30] mutation is as follows:

(SEQ ID NO: 20)
```
  1 mgmacltmte megtstssiy qngdisgnan smkqidpvlq vylyhslgks eadyltfpsg 61 eyvaeeicia askacgitpv yhnmfalmse teriwyppnh vfhidestrh nvlyrirfyf 121 prwycsgsnr ayrhgisrga eaplldddfvm sylfaqwrhd fvhgwikvpv thetqeeclg 181 mavldmmria kendqtplai ynsisyktfl pkcirakiqd yhiltrkrir yrfrrfiqqf 241 sqckatarnl klkylinlet lqsafytekf evkepgsgps geeifatiii tgnggiqwsr 301 gkhkesetlt eqdlqlycdf pniidvsikq anqegsnesr vvtihkqdgk nleielsslr 361 ealsfvslid gyyrltadah hylckevapp avleniqsnc hgpismdfai sklkkagnqt 421 glyvlrcspk dfnkyfltfa verenvieyk hclitknene eynlsgtkkn fsslkdllnc 481 yqmetvrsdn iifqftkccp pkpkdksnll vfrtngvsdv ptsptlqrpt hmnqmvfhki 541 rnedlifnes lgqgtftkif kgvrrevgdy gqlhetevll kvldkahrny sesffeaasm 601 msklshkhlv lnygvcfcgd enilvqefvk fgsldtylkk nkncinilwk levakqlawa 661 mhfleentli hgnvcaknil lireedrktg nppfiklsdp gisitvlpkd ilqeripwvp 721 pecienpknl nlatdkwsfg ttlweicsgg dkplsaldsq rklqfyedrh qlpapkwael 781 anlinncmdy epdfrpsfra iirdlnslft pdyelltend mlpnmrigal gfsgafedrd 841 ptqfeerhlk flqqlgkgnf gsvemcrydp lqdntgevva vkklqhstee hlrdfereie 901 ilkslqhdni vkykgvcysa grrnlklime ylpygslrdy lqkhkeridh ikllgytsqi 961 ckgmeylgtk ryihrdlatr nilvknenrv kigdfgltkv lpqdkeyykv kepgespifw 1021 yapesltesk fsvasdvwsf gvvlyelfty iekskspppae fmrmigndkq gqmivfhlie 1081 llknngrlpr pdgcpdeiym imtecwnnnv nqrpsfrdla lrvdqirdnm ag
```

The ordinarily skilled artisan could readily determine the nucleotide sequences (i.e. mRNA) that encode the JAK2V617F polypeptide mutants described above.

Cells containing these mutations had a 9 to 33-fold higher $EC_{50}$ for ruxolitinib compared to native JAK2V617F. The results described herein further indicate that these mutations also confer cross-resistance to all JAK2 kinase inhibitors tested, including AZD1480, TG101348, lestaurtinib (CEP-701) and CYT-387. Surprisingly, introduction of the 'gatekeeper' mutation (M929I) in JAK2V617F affected only ruxolitinib sensitivity (4-fold increase in $EC_{50}$). These results indicate that JAK2 inhibitors currently in clinical trials are prone to resistance as a result of point mutations and caution should be exercised when administering these drugs. Thus, this finding has dramatic implications for the therapy of patients with myeloproliferative neoplasms. It serves as both a positive and negative predictive test and thus allows clinicians to better focus the use of these expensive and toxic agents to that subset of the population the greatest potential chance of benefit as early as possible.

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as "clinical parameters" defined herein, as well as "traditional laboratory risk factors", also defined herein. Biomarkers also include any calculated indices created mathematically or combinations of any one or more of the foregoing measurements, including temporal trends and differences. Where available, and unless otherwise described herein, biomarkers which are gene products are identified based on the official letter abbreviation or gene symbol assigned by the international Human Genome Organization Naming Committee (HGNC) and listed at the date of this filing at the US National Center for Biotechnology Information (NCBI) web site.

A "Clinical indicator" is any physiological datum used alone or in conjunction with other data in evaluating the physiological condition of a collection of cells or of an organism. This term includes pre-clinical indicators.

"Clinical parameters" encompasses all non-sample or non-analyte biomarkers of subject health status or other characteristics, such as, without limitation, age (Age), ethnicity (RACE), gender (Sex), or family history (FamHX).

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining biomarkers are linear and non-linear equations and statistical classification analyses to determine the relationship between biomarkers detected in a subject sample and the subject's responsiveness to chemotherapy. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or B ayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis An Example Showing The Relationships Among Serum Lipid And Apolipoprotein Concentrations In Identifying Subjects With Coronary Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the responsiveness to treatment, cancer recurrence or survival and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation" or "evaluation of risk" in the context of the present invention encompasses making a prediction of the probability, odds, or likelihood that an event or disease state may occur, the rate of occurrence of the event or conversion from one disease state. Risk evaluation can also comprise prediction of future clinical parameters, traditional laboratory risk factor values, or other indices of cancer, either in absolute or relative terms in reference to a previously measured population. The methods of the present invention may be used to make continuous or categorical measurements of the responsiveness to treatment thus diagnosing and defining the risk spectrum of a category of subjects defined as being responders or non-responders. In the categorical scenario, the invention can be used to discriminate between normal and other subject cohorts at higher risk for responding. Such differing use may require different biomarker combinations and individualized panels, mathematical algorithms, and/or cut-off points, but be subject to the same aforementioned measurements of accuracy and performance for the respective intended use.

A "sample" in the context of the present invention is a biological sample isolated from a subject and can include, by way of example and not limitation, tissue biopies, whole blood, serum, plasma, blood cells, endothelial cells, lymphatic fluid, ascites fluid, interstitital fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids. A "sample" may include a single cell or multiple cells or fragments of cells. The sample is also a tissue sample. The sample is or contains a circulating endothelial cell or a circulating tumor cell. The sample includes a primary tumor cell, primary tumor, a recurrent tumor cell, or a metastatic tumor cell.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is considered highly significant at a p-value of 0.05 or less. Preferably, the p-value is 0.04, 0.03, 0.02, 0.01, 0.005, 0.001 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of cancer. A subject can be male or female.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms. Traditional laboratory risk factors for tumor recurrence include for example Proliferative index, tumor infiltrating lymphocytes. Other traditional laboratory risk factors for tumor recurrence known to those skilled in the art.

Methods and Uses of the Invention

The methods disclosed herein are used with subjects undergoing treatment and/or therapies for myeloproliferative neoplasms, subjects who are at risk for developing a reoccurrence of a myeloproliferative neoplasm, and subjects who have been diagnosed with a myeloproliferative neoplasm. The methods of the present invention are to be used to monitor or select a treatment regimen for a subject who has a myeloproliferative neoplasm, and to evaluate the predicted survivability and/or survival time of a cancer-diagnosed subject. Treatment regimens include JAK inhibitor therapy such as ruxolitinib, CYT-387, TG101348, AZD1480, or lestaurtinib.

Responsiveness (e.g., resistance or sensitivity) of a cell to JAK inhibitor therapy is determined by detecting a mutation associated with responsiveness to JAK inhibitor therapy in a test sample (e.g., a subject derived sample). The mutation associated with responsiveness to JAK inhibitor therapy includes a somatic mutation in the JAK2V617F gene leading to an amino acid substitution at positions 931, 935, 938, 960 and/or 985 of the JAK2V617F polypeptide. Specifically, these mutations results in a tyrosine to a cysteine at position 931 (Y931C); a glycine to an arginine at position 935 (G935R); an arginine to a leucine at position 938 (R938L); an isoleucine to a valine at position 960 (I960V), and a glutamic acid to a lysine at position 985 (E985K). These mutations are referred to herein as JAK2 JH1 domain mutations.

The presence of one or more of these JAK2 JH1 domain mutations indicates the cell will be non-responsive (i.e., resistant) to JAK inhibitor therapy. In contrast, the absence any of these mutations indicates the cell will be responsive (i.e., sensitive) to JAK inhibitor therapy.

The cell is for example a cancer cell. Optionally, the cancer is a myeloproliferative neoplasms, such as polycythemia vera, essential thrombocythemia, idiopathic myelofibrosis, acute myeloid leukemia or a myelodysplastic syndrome.

By resistance it is meant that a cell fails to respond to an agent or responds with reduced efficacy. For example, resistance to JAK inhibitor therapy means the cell is not damaged or killed by the drug. By sensitivity it is meant that that the cell responds to an agent. For example, sensitivity to JAK inhibitor therapy means the cell is damaged or killed by the drug. The cell is a cancer cell, for example, a cancer cell from myeloproliferative neoplasms.

The methods of the present invention are useful to treat, alleviate the symptoms of, monitor the progression of or delay the onset of cancer.

Preferably, the methods of the present invention are used to identify and/or diagnose subjects who are asymptomatic for a cancer recurrence. "Asymptomatic" means not exhibiting the traditional symptoms.

The methods of the present invention are also useful to identify and/or diagnose subjects already at higher risk of developing JAK2V617F myeloid malignancies or based on solely on the traditional risk factors.

Identification of the mutations allows for the determination of whether a subject will derive a benefit from a particular course of treatment. In this method, a biological sample is provided from a subject before undergoing treatment, e.g., JAK inhibitor therapy, chemotherapy, radiotherapy, or any other cancer therapy or combinations thereof. By "derive a benefit" it is meant that the subject will respond to the course of treatment. By responding it is meant that the treatment decreases in size, prevalence, or metastatic potential of a cancer in a subject. When treatment is applied prophylactically, "responding" means that the treatment retards or prevents a cancer recurrence from forming, or retards, prevents, or alleviates a symptom. Assessment of cancers is made using standard clinical protocols.

The present invention provides methods for selecting a treatment regimen for a subject, including detecting the presence or absence of detecting the presence or absence of one or more point mutations in the kinase domain of the JAK2V617F polypeptide. The mutations are at amino acids 931, 935, 938, 960, and/or 985. Preferably the one or more point mutations are selected from the group consisting of Y931C, G935R, R938L, I960V, and E985K in the kinase domain of the JAK2V617F polypeptide. The absence of the mutation indicates the subject should receive JAK inhibitor treatment. The presence of the mutation indicates the subject should not receive JAK inhibitor treatment.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like cancer, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

Differences in the genetic makeup of subjects can result in differences in their relative abilities to metabolize various drugs, which may modulate the symptoms or risk factors of cancer or metastatic events. Subjects that have cancer, or are at risk for developing cancer or a metastatic event can vary in age, ethnicity, and other parameters. Accordingly, detection of the mutations disclosed herein, both alone and together in combination with known genetic factors for drug metabolism, allow for a pre-determined level of predictability that a putative therapeutic or prophylactic to be tested in a selected subject will be suitable for treating cancer in the subject.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic, predictive, or prognostic test, assay, or method concerns the ability of the test, assay, or method to distinguish between subjects responsive to chemotherapeutic treatment and those that are not, is based on whether the subjects have a JAK2 JH1 domain mutation.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for therapeutic unresponsiveness, and the bottom quartile comprising the group of subjects having the lowest relative risk for therapeutic unresponsiveness. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future events. Often such lower diagnostic accuracy tests must be combined with additional parameters in order to derive meaningful clinical thresholds for therapeutic intervention, as is done with the aforementioned global risk assessment indices.

A health economic utility function is yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

Detection of a JAK2 JH1 Domain Mutation

The actual detection of the JAK2 JH1 domain mutation can be determined at the protein or nucleic acid level using any method known in the art.

JAK2 JH1 domain mutation-specific reagents useful in the practice of the disclosed methods include, among others, mutant polypeptide specific antibodies and AQUA peptides (heavy-isotope labeled peptides) corresponding to, and suitable for detection and quantification of, mutant polypeptide expression in a biological sample. A mutant polypeptide-specific reagent is any reagent, biological or chemical, capable of specifically binding to, detecting and/or quantifying the presence/level of expressed mutant polypeptide in a biological sample, while not binding to or detecting wild type. The term includes, but is not limited to, the preferred antibody and AQUA peptide reagents discussed below, and equivalent reagents are within the scope of the present invention.

Reagents suitable for use in practice of the methods of the invention include a mutant polypeptide-specific antibody. A mutant-specific antibody of the invention is an isolated antibody or antibodies that specifically bind(s) a mutant polypeptide of the invention, but does not substantially bind either wild type or when mutated at other positions.

Mutant polypeptide-specific antibodies generated against human mutant may also bind to highly homologous and equivalent epitopic peptide sequences in other mammalian species, for example murine, rat, feline, pig, or rabbit, and vice versa. Antibodies useful in practicing the methods of the invention include (a) monoclonal antibodies, (b) purified polyclonal antibodies that specifically bind to the target polypeptide (e.g. an epitope comprising the mutation point, (c) antibodies as described in (a)-(b) above that bind equivalent and highly homologous epitopes or phosphorylation sites in other non-human species (e.g. mouse, rat), and (d) fragments of (a)-(c) above that bind to the antigen (or more preferably the epitope) bound by the exemplary antibodies disclosed herein.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., Molec. Immunol. 26: 403-11 (1989); Morrison et al., Proc. Nat'l. Acad. Sci. 81:6851 (1984); Neuberger et al., Nature 312:604 (1984)). The antibodies may be recombinant monoclonal antibodies produced according to the methods disclosed in U.S. Pat. No. 4,474,893 (Reading) or U.S. Pat. No. 4,816,567 (Cabilly et al.). The antibodies may also be chemically constructed specific antibodies made according to the method disclosed in U.S. Pat. No. 4,676,980 (Segel et al.).

The invention is not limited to use of antibodies, but includes equivalent molecules, such as protein binding domains or nucleic acid aptamers, which bind, in a mutant-protein or truncated-protein specific manner, to essentially the same epitope to which a mutant polypeptide-specific antibody useful in the methods of the invention binds. See, e.g., Neuberger et al., Nature 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired mutant-protein specific epitope (e.g. the sequence comprising the mutation site) collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, Methods In Enzymology, 201:264-283 (1991); Merrifield, J. Am. Chem. Soc. 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. Nature 265:495-97 (1975); Kohler and Milstein, Eur. J. Immunol. 6: 511 (1976); see also, CURRENT PROTOCOLS IN MOLECULAR BIOLOGY, Ausubel et al., Eds. (1989). Monoclonal antibodies so produced are highly specific, and improve the selectivity and specificity of assay methods provided by the invention. For example, a solution containing the appropriate antigen (e.g. a synthetic peptide comprising the mutant junction of mutant polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit mutant hybridomas, for example, may be produced as described in U.S. Pat. No. 5,675,063, K. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below.

The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, Science 246:1275-81 (1989); Mullinax et al., Proc. Nat'l Acad. Sci. 87: 8095 (1990). If monoclonal antibodies of one isotype are preferred for a particular application, particular isotypes can be prepared directly, by selecting from the initial mutant, or prepared secondarily, from a parental hybridoma secreting a monoclonal antibody of different isotype by using the sib selection technique to isolate class-switch variants (Steplewski, et al., Proc. Nat'l. Acad. Sci., 82:8653 (1985); Spira et al., J. Immunol. Methods, 74.307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al., (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and mutant protein specificity according to standard techniques. See, e.g. Czernik et al., Methods in Enzymology, 201: 264-283 (1991). For example, the antibodies may be screened against a peptide library by ELISA to ensure specificity for both the desired antigen and, if desired, for reactivity only with a mutant polypeptide of the invention and not with wild type. The antibodies may also be tested by Western blotting against cell preparations containing target protein to confirm reactivity with the only the desired target and to ensure no appreciable binding to other mutants not containing the point mutation. The production, screening, and use of mutant protein-specific antibodies are known to those of skill in the art, and have been described.

Mutant polypeptide-specific antibodies useful in the methods of the invention may exhibit some limited cross-reactivity with similar epitopes in other highly homologous proteins. This is not unexpected as most antibodies exhibit some degree of cross-reactivity, and anti-peptide antibodies will often cross-react with epitopes having high homology or identity to the immunizing peptide. See, e.g., Czernik, supra. Gross-reactivity with other mutant proteins is readily characterized by Western blotting alongside markers of known molecular weight. Amino acid sequences of cross-reacting proteins may be examined to identify sites highly homologous or identical to the mutant polypeptide sequence to which the antibody binds. Undesirable cross-reactivity can be removed by negative selection using antibody purification on peptide columns (e.g. selecting out antibodies that bind either wild type polypeptide or which bind highly homologous sequences on different proteins).

Mutant polypeptide-specific antibodies of the invention that are useful in practicing the methods disclosed herein may specifically bind to JAK2V617F with mutations at amino acid positions 931, 935, 938, 960, and/or 985. Particularly preferred are mutant polypeptide-specific antibodies that specifically bind to a mutant JAK2 polypeptide with any of the following mutations: Y931C, G935R, R938L, I960V, and/or E985K. In another preferred embodiment, the mutant polypeptide-specific antibodies of the present invention do not recognize or bind to JAK polypeptides that do not contain mutations at amino acid positions 931, 935, 938, 960, and/or 985. These antibodies are useful in the methods described herein for distinguishing subjects with JAK2V617F and mutations at amino acids 931, 935, 938, 960, and/or 985, wherein the presence of mutant JAK2 with these mutations indicates that the subject may develop or has developed resistance to JAK inhibitor therapies, such as JAK kinase inhibitors. Thus, the presence of mutant JAK2 V617F by mutant polypeptide-specific antibodies would indicate that a therapy that does not utilize JAK inhibitors should be used to treat the subject.

Mutant polypeptide-specific antibodies of the invention that are useful in practicing the methods disclosed herein are ideally specific for human mutant polypeptide, but are not limited only to binding the human species, per se. The invention includes the production and use of antibodies that also bind conserved and highly homologous or identical epitopes in other mammalian species (e.g. mouse, rat, monkey). Highly homologous or identical sequences in other species can readily be identified by standard sequence comparisons, such as using BLAST, with the human mutant polypeptide sequence the proteins sequences from other mammalian species have been published and are available in the SwissProt database.

Antibodies employed in the methods of the invention may be further characterized by, and validated for, use in a particular assay format, for example FC, IHC, and/or ICC. The use of mutant polypeptide-specific antibodies in such methods is further described below. Antibodies may also be advantageously conjugated to fluorescent dyes (e.g. Alexa488, PE), or labels such as quantum dots, for use in multi-parametric analyses along with other signal transduction (phospho-AKT, phospho-Erk 1/2) and/or cell marker (cytokeratin) antibodies, as further described below.

In practicing the methods of the invention, the expression and/or activity of wild type in a given biological sample may also be advantageously examined using antibodies (either phospho-specific or total) for these wild type proteins. Such antibodies may also be produced according to standard methods, as described above. The amino acid sequences of human are published, as are the sequences of these proteins from other species, including mammalian, as noted above.

Detection of wild type expression and/or activation, along with mutant polypeptide expression, in a biological sample (e.g. a tumor sample) can provide information on whether the mutant protein alone is driving the tumor, or whether wild type is also activated and driving the tumor. Such information is clinically useful in assessing whether targeting the mutant protein or the wild type protein(s), or both, or is likely to be most beneficial in inhibiting progression of the tumor, and in selecting an appropriate therapeutic or combination thereof.

It will be understood that more than one antibody may be used in the practice of the above-described methods. For example, one or more mutant polypeptide-specific antibodies together with one or more antibodies specific for another protein, receptor, that is suspected of being, or potentially is, activated in a cancer in which mutant polypeptide is expressed may be simultaneously employed to detect the activity of such other signaling molecules in a biological sample comprising cells from such cancer.

Those of skill in the art will appreciate that mutant polypeptides of the present invention and the mutant junction epitope-bearing fragments thereof described above can be combined with parts of the constant domain of immunoglobulins (IgG), resulting in chimeric polypeptides. These mutant proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331: 84-86 (1988)). Mutant proteins that have a disulfide-linked dimeric structure due to the IgG part can also be more efficient in binding and neutralizing other molecules than the monomeric mutant polypeptide alone (Fountoulakis et al., J Biochem 270: 3958-3964 (1995)).

Mutant polypeptide-specific reagents useful in the practice of the disclosed methods may also comprise heavy-isotope labeled peptides suitable for the absolute quantification of expressed mutant polypeptide in a biological sample. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al., Proc. Natl. Aced. Sci. U.S.A. 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immuno-affinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{2}H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry (MS) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or MSn spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra. AQUA internal peptide standards (heavy-isotope labeled peptides) may desirably be produced, as described above, to detect and quantify any unique site (e.g. the mutation point) within a mutant polypeptide of the invention. For example, an AQUA phosphopeptide may be prepared that corresponds to the peptide sequence immediately encompassing the mutation point. Peptide standards may be produced and such standards employed in the AQUA methodology to detect and quantify the presence of mutant JAK2 (i.e. the presence of the peptide sequence encompassing the point mutation) in a biological sample.

For example, an exemplary AQUA peptide of the invention comprises the amino acid sequence EVA, which corresponds to the three amino acids immediately flanking each side of the mutation point in the mutant JAK2 polypeptide. It will be appreciated that larger AQUA peptides comprising the mutant junction sequence (and additional residues downstream or upstream of it) may also be constructed. Similarly, a smaller AQUA peptide comprising less than all of the residues of such sequence (but still comprising the point of mutant junction itself) may alternatively be constructed. Such larger or shorter AQUA peptides are within the scope of the present invention, and the selection and production of preferred AQUA peptides may be carried out as described above (see Gygi et al., Gerber et al., supra.).

Mutant-specific reagents provided by the invention also include nucleic acid probes and primers suitable for detection of a mutant polynucleotide. The specific use of such probes in assays such as fluorescence in-situ hybridization (FISH) or polymerase chain reaction (PCR) amplification.

Also provided by the invention is a kit for the detection of mutant JAK2 in a biological sample, the kit comprising an isolated mutant-specific reagent of the invention and one or more secondary reagents. Suitable secondary reagents for employment in a kit are familiar to those of skill in the art, and include, by way of example, buffers, detectable secondary antibodies or probes, activating agents, and the like.

The methods of the invention may be carried out in a variety of different assay formats known to those of skill in the art.

Immunoassays useful in the practice of the methods of the invention may be homogenous immunoassays or heterogeneous immunoassays. In a homogeneous assay the immunological reaction usually involves a mutant polypeptide-specific reagent (e.g. a mutant Polypeptide-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semiconductor nanocrystal labels, or "quantum dots", may also be advantageously employed, and their preparation and use has been well described. See generally, K. Barovsky, Nanotech. Law & Bus. 1 (2): Article 14 (2004) and patents cited therein.

In a heterogeneous assay approach, the reagents are usually the biological sample, a mutant polypeptide-specific reagent (e.g., a mutant-specific antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. Mutant polypeptide-specific monoclonal antibodies may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of mutant polypeptide is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other mutant polypeptide-binding reagents may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), or immunofluorescence (IF) are particularly desirable in practicing the methods of the invention, since such assay formats are clinically-suitable, allow the detection of mutant polypeptide expression in vivo, and avoid the risk of artifact changes in activity resulting from manipulating cells obtained from, e.g. a tumor sample in order to obtain extracts. Accordingly, in some preferred embodiment, the methods of the invention are implemented in a flow-cytometry (FC), immuno-histochemistry (IHC), or immunofluorescence (IF) assay format.

Flow cytometry (FC) may be employed to determine the expression of mutant polypeptide in a mammalian leukemia sample before, during, and after treatment with a drug targeted at inhibiting activity. For example, tumor cells from a bone marrow sample may be analyzed by flow cytometry for mutant polypeptide expression and/or activation, as well as for markers identifying cancer cell types, etc., if so desired. Flow cytometry may be carried out according to standard methods. See, e.g. Chow et al., Cytometry (Communications in Clinical Cytometry) 46: 72-78 (2001). Briefly and by way of example, the following protocol for cytometric analysis may be employed: fixation of the cells with 2% paraformaldehyde for 10 minutes at 37.degree. C. followed by permeabilization in 90% methanol for 30 minutes on ice. Cells may then be stained with the primary mutant polypeptide-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed mutant polypeptide in the tumor.

Immunohistochemical (IHC) staining may be also employed to determine the expression and/or activation status of mutant polypeptide in a mammalian cancer (e.g. AML) before, during, and after treatment with a drug targeted at inhibiting activity. IHC may be carried out according to well-known techniques. See, e.g., ANTIBODIES; A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-mutant polypeptide antibody and secondary antibody; and finally detecting using ABC avidin/biotin method according to manufacturer's instructions.

Immunofluorescence (IF) assays may be also employed to determine the expression and/or activation status of mutant polypeptide in a mammalian cancer before, during, and after treatment with a drug targeted at inhibiting activity. IF may be carried out according to well-known techniques. See, e.g., J. M. Polak and S. Van Noorden (1997) INTRODUC- TION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against mutant polypeptide followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (, phospho-AKT, phospho-Erk 1/2) and/or cell marker (cytokeratin) antibodies.

A variety of other protocols, including enzyme-linked immunosorbent assay (ELISA), radio-Immunoassay (RIA), and fluorescent-activated cell sorting (FACS), for measuring mutant polypeptide are known in the art and provide a basis for diagnosing altered or abnormal levels of mutant polypeptide expression. Normal or standard values for mutant polypeptide expression are established by combining body fluids or cell extracts taken from normal mammalian subjects, preferably human, with antibody to mutant polypeptide under conditions suitable for complex formation. The amount of standard complex formation may be quantified by various methods, but preferably by photometric means. Quantities of mutant polypeptide expressed in subject, control, and disease samples from biopsied tissues are compared with the standard values. Deviation between standard and subject values establishes the parameters for diagnosing disease.

Similarly, AQUA peptides for the detection/quantification of expressed mutant polypeptide in a biological sample comprising cells from a tumor may be prepared and used in standard AQUA assays, as described in detail i above. Accordingly, in some preferred embodiments of the methods of the invention, the mutant polypeptide-specific reagent comprises a heavy isotope labeled phosphopeptide (AQUA peptide) corresponding to a peptide sequence comprising the mutant junction of mutant polypeptide, as described above.

Mutant polypeptide-specific reagents useful in practicing the methods of the invention may also be mRNA, oligonucleotide or DNA probes that can directly hybridize to, and detect, mutant or truncated polypeptide expression transcripts in a biological sample. Briefly, and by way of example, formalin-fixed, paraffin-embedded patient samples may be probed with a fluorescein-labeled RNA probe followed by washes with formamide, SSC and PBS and analysis with a fluorescent microscope.

Polynucleotides encoding mutant polypeptide may also be used for diagnostic purposes. The polynucleotides that may be used include oligonucleotide sequences, antisense RNA and DNA molecules. The polynucleotides may be used to detect and quantitate gene expression in biopsied tissues in which expression of mutant polypeptide or truncated active polypeptide may be correlated with disease. For example, the diagnostic assay may be used to distinguish between absence, presence, and excess expression of mutant polypeptide, and to monitor regulation of mutant polypeptide levels during therapeutic intervention.

In one preferred embodiment, hybridization with PCR probes which are capable of detecting polynucleotide sequences, including genomic sequences, encoding mutant polypeptide or truncated active polypeptide, or closely related molecules, may be used to identify nucleic acid sequences which encode mutant polypeptide. The construction and use of such probes is described above. The specificity of the probe, whether it is made from a highly specific region, e.g., 10 unique nucleotides in the mutant junction, or a less specific region, e.g., the 3' coding region, and the stringency of the hybridization or amplification (maximal, high, intermediate, or low) will determine whether the probe identifies only naturally occurring sequences encoding mutant polypeptide, alleles, or related sequences.

Probes may also be used for the detection of related sequences, and should preferably contain at least 50% of the nucleotides from any of the mutant polypeptide encoding sequences. The hybridization probes of the subject invention may be DNA or RNA and derived from the nucleotide sequence and encompassing the mutation point, or from genomic sequence including promoter, enhancer elements, and introns of the naturally occurring polypeptides but comprising the mutation point sequence.

A mutant polynucleotide or truncated polynucleotide of the invention may be used in Southern or northern analysis, dot blot, or other membrane-based technologies; in PCR technologies; or in dip stick, pin, ELISA or chip assays utilizing fluids or tissues from patient biopsies to detect altered polypeptide expression. Such qualitative or quantitative methods are well known in the art. Mutant polynucleotides may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding mutant polypeptide in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease characterized by expression of mutant polypeptide, a normal or standard profile for expression is established. This may be accomplished by combining body fluids or cell extracts taken from normal subjects, either animal or human, with a sequence, or a fragment thereof, which encodes mutant polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for mutant polynucleotides of the invention may involve the use of polymerase chain reaction (PCR), a preferred assay format that is standard to those of skill in the art. See, e.g., MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989). PCR oligomers may be chemically synthesized, generated enzymatically, or produced from a recombinant source. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of mutant polypeptide include radiolabeling or biotinylating nucleotides, coamplification of a control nucleic acid, and standard curves onto which the experimental results are interpolated (Melby et al., J. Immunol. Methods, 159:235-244 (1993); Duplaa et al. Anal. Biochem. 229-236 (1993)). The speed of quantitation of multiple samples may be accelerated by running the assay in an ELISA format where the oligomer of interest is presented in various dilutions and a spectrophotometric or calorimetric response gives rapid quantitation.

Other suitable methods for nucleic acid detection, such as minor groove-binding conjugated oligonucleotide probes (see, e.g. U.S. Pat. No. 6,951,930, "Hybridization-Triggered Fluorescent Detection of Nucleic Acids") are known to those of skill in the art.

Other suitable methods for detection of the mutant nucleotide sequence include RT-PCR, next generation sequencing (i.e., Illumina® or Solexa® sequencing, 454 pyrosequencing), and Nanostring® technologies.

EXAMPLES

Example 1. Identification of Novel Mutations in JAK2V617F that CAUse Ruxolitinib Resistance A screen was performed to identify ruxolitinib resistant JAK2V617F mutations using a mutagenesis strategy with a repair deficient *E. coli* strain, similar to previously described approaches. The approach was specifically designed to look for mutations in the predicted drug binding region of JAK2.

Random Mutagenesis of JAK2V617F.

Random mutations were introduced into the pMSCV.JAK2V617F.IRES.GFP construct using the mutT (unable to hydrolyze 8-oxodGTP), mutS (error-prone mismatch repair) and mutD (deficient in 3'- to 5'-exonuclease of DNA polymerase III) deficient XL1-Red *E. coli* strain, according to the manufacturer's protocol (Agilent, Santa Clara, Calif.). A total of seven different libraries of mutagenized JAK2V617F expression vectors were generated and expressed in BaF3.EpoR cells.

Cell Culture.

The murine pre-B BaF3 cell line expressing the erythropoietin receptor (EpoR) was maintained in RPMI 1640 (Mediatech, Manassas, Va.) containing 10% fetal bovine serum (FBS; Lonza, Walkersville, Md.), supplemented with WEHI-3B conditioned medium under a 5% CO2 atmosphere. Cell growth in response to various drug concentrations was measured by trypan blue (Sigma) exclusion or with the CellTiter 96® AQueous One Solution Cell Proliferation Assay reagent (Promega, Madison, Wis.). The CalcuSyn (Biosoft, Great Shelford, United Kingdom) analysis program was used to estimate drug concentrations resulting in 50% inhibition (EC50), compared to control treated cells.

Identification of Cells Resistant to Ruxolitinib.

Mutagenized JAK2V617F libraries were used to prepare retroviral supernatants 6 to infect BaF3 cells expressing the erythropoietin receptor (BaF3.EpoR). Cells were expanded for at least three days and pretreated with 1.44 μM ruxolitinib (12 times the EC50 in parental cells) for two days before sorting of single GFP-expressing cells into 96-well plates. Resistant colonies were isolated in the presence of 1.44 μM ruxolitinib.

Detection of Mutations in the Kinase Domain.

Genomic DNA was isolated (QIAmp DNA Blood kit, Qiagen, Germantown, Md.) from drug resistant colonies and the putative drug binding region in the kinase domain amplified by PCR (AccuPrime Pfx, Invitrogen, Carlsbad, Calif.) using standard methods and specific primers (forward: 5'-ATGAGCCAGATTTCAGGCCTGCTT-3' (SEQ ID NO: 3); reverse 5'-AGAAAGTTGGGCATCACGCA-GCTA-3' (SEQ ID NO: 4)) on a MJ Research PTC-200 Peltier Thermal Cycler (St. Bruno, Canada). DNA sequencing was performed at the DFCI Molecular Biology Core Facility (forward PCR primer or 5'-ACATGAGAATAGGT-GCCCTAGG-3' (SEQ ID NO: 5)) and ambiguous results were confirmed by sequencing of the reverse strand (not shown). Identified mutations were reintroduced into JAK2V617F by site-directed mutagenesis using the QuikChange II XL Mutagenesis Kit (Agilent) and specific mutagenesis primers, according to the manufacturer's protocol. The entire cDNA sequence of the mutagenized product was verified by DNA sequencing.

In preliminary experiments, resistant clones were initially selected at 3-, 6- and 12-times the EC50 of ruxolitinib (0.36 μM, 0.72 μM and 1.44 μM, respectively). Only the highest ruxolitinib (1.44 μM) concentration was sufficient to allow for the identification of resistant mutations at a frequency >10% of total. 128 independent resistant clones were isolated, but the majority of clones did not contain a mutation in the sequenced region and the mechanism of resistance was not further investigated. Overall, five different point mutations, including Y931C (Tyr931Cys), G935R (Gly935Arg), R938L (Arg938Leu), I960V (Ile960Val) and E985K (Glu985Lys) were identified (FIG. 1A, right).

Example 2. Structural Analysis of JAK2V617F Kinase Domain Mutations

The three-dimensional structure of ruxolitinib (PubChem: CID 25126798) was docked onto the monomer three-dimensional structure of JAK2 extracted from the CMP6-bound JAK2 crystal structure (PDB ID: 2B7A).

Analysis

Docking calculations were carried out using Docking-Server. Gasteiger partial charges were added to the ligand atoms. Non-polar hydrogen atoms were merged, and rotatable bonds were defined. Essential hydrogen atoms, Kollman united atom type charges, and solvation parameters were added with the aid of AutoDock tools. To limit the docking simulations to the inhibitor-binding pocket, determined from the CMP6-JAK2 structure, the affinity grid was set to fit the inhibitor-binding pocket. AutoDock parameter set- and distance-dependent dielectric functions were used in the calculation of the van der Waals and the electrostatic terms, respectively. Docking simulations were performed using the Lamarckian genetic algorithm (LGA) and the Solis & Wets local search method as applied in the Docking-Server. Initial position, orientation, and torsions of the ligand molecules were set randomly. All rotatable torsions were released during docking. Each docking experiment was derived from 2 different runs that were set to terminate after a maximum of 250,000 energy evaluations. The population size was set to 150. During the search, a translational step of 0.2 Å, and quatemion and torsion steps of 5 were applied. The best scoring docking pose of ruxolitinib-JAK2 was used for the drug-target interface analysis in PyMOL (www.pymol.org) and structure figures were rendered using PyMOL.

Published structures of JAK2 bound to CMP6 and CP690, 550 provide important clues on the mode of binding and interactions between the related JAK2 inhibitors and the protein. Both CMP6 and CP690,550 bind in the ATP-binding pocket of JAK2. The parameters were set to preferentially simulate ruxolitinib docking positions in the CMP6 and CP690,550 binding pocket on JAK2. The best scoring docking pose, with least estimated free energy of binding (−9.05 kCal/mol), best estimated inhibition constant (KI of 231.83 nM) and highest interaction interface area (567.6 Å2), was used for the inhibitor-JAK2 interface analysis.

Ruxolitinib snugly fits into the ATP-binding pocket of JAK2 similar to CMP6 and CP690,550, with the cyclopentyl and pyrazol rings tightly fitting in the deep hydrophobic groove (FIG. 1A). JAK2-ruxolitinib interaction interface buries most of the surface area of the inhibitor. The inhibitor is held in the pocket by polar contacts between cyclopentyl ring and main chain atoms in the hinge region (between Y931 and L932), and also pyrrolopyrimidine moiety with N981 sidechain. Ruxolitinib may also form hydrogen bonds with water molecules in the pocket.

Ruxolitinib makes extensive hydrophobic interactions with several residues that line the binding pocket, similar to what was observed for CMP6 and CP690,550. A880, L855, V863 and M929 hold the inhibitor tight from the top and L932 in the hinge region holds it from the side. Further, V911 and L983 provide hydrophobic interactions from the bottom (FIG. 1B, left panel). The pyrazol ring of ruxolitinib is in a distance to have π-π interaction with the Y931 ring. Most mutations that were identified in our screen are either interacting residues with ruxolitinib or in proximity of the binding pocket (FIG. 1B, right panels) and hence are likely to alter the inhibitor binding. Y931 seems to be a critical residue for inhibitor-protein interaction as its side chain and mainchain atoms have interactions with the inhibitor. The Y931C mutation might disrupt the π-π interaction between tyrosine ring and the inhibitor ring structure, thus weakening the inhibitor binding and resulting in easy expulsion from the pocket. The G935R mutation pushes a large charged sidechain towards the mouth of the hydrophobic cavity (FIG. 1B, right), which results in a strong positive charge at the corner of the binding pocket, compared to the native protein (FIG. 1C). The exact mechanism by which the R938L (FIG. 1B, right) and I960V mutations may affect the inhibitor binding cannot easily be explained based on the computational analysis of the structure, but these two residues lie near the binding pocket (R938L at the end of the hinge region and I960V in close proximity of the binding pocket). The E985K mutation could bring the sidechain very close to the inhibitor-binding site and result in charge repulsion of the inhibitor.

Example 3. Ruxolitinib-Resistant Mutations Display Cross-Resistance to Other JAK2 Tyrosine Kinase Inhibitors The identified mutants were reintroduced into JAK2V617F and expressed in BaF3.EpoR cells to confirm that the mutants truly conferred drug resistance.

Characterization of Cell Lines Expressing Mutated JAK2V617F.

BaF3.EpoR cell lines expressing potential drug resistant mutant JAK2V617F were generated by retroviral infection, as described previously. Stable transfectants were sorted for GFP+ cells and the presence of the mutation confirmed by DNA sequencing of the putative drug-binding site, as described above. Polyclonal populations of these cells were used to determine changes in growth in response to various JAK2 inhibitors. All cell lines generated, spontaneously converted into growth factor independence.

Consistent with the structural analysis, both the Y931C and G935R mutations resulted in the largest increase (33.3-fold and 19.5-fold, respectively) in EC50 values, compared to native JAK2V617F (FIG. 2A). The increase in EC50 values of ruxolitinib for the R938L (12.7-fold), I960V (11.5-fold) and the E985K (9.0-fold) mutation containing cells was somewhat lower. These data are also consistent with the screening approach, which allowed survival and outgrowth of resistant colonies at 1.44 µM ruxolitinib.

The effect of the mutations on the sensitivity of other JAK2 tyrosine kinase inhibitors was assayed (FIG. 2). In contrast to ruxolitinib, there was a comparable increase in drug resistance for all mutations in response to CYT-387 (5.1 to 7.4-fold increase in EC50) (FIG. 2B), TG101348 (2.2 to 2.8-fold increase in EC50) (FIG. 2C), and Lestaurtinib (2.6 to 3.3-fold increase in EC50) (FIG. 2E). The changes in EC50 in response to AZD1480 were qualitatively similar to ruxolitinib (FIG. 2D). Both, the Y931C and G935R mutations had the highest EC50 values (>10 µM), corresponding to a >7-fold increase in EC50. Also, like ruxolitinib, lower EC50 values for AZD1480 were found with R938L, I960V and E985K (5.6 to 6.5-fold increase) mutation containing cells (FIG. 2D).

Example 4. Ruxolitinib Resistance Confers a Growth Advantage During JAK2 Inhibition Resistant mutations confer a growth advantage in the presence of ruxolitinib. JAK2V617F expressing cells were co-cultured with a defined amount of cells containing the E985K or Y931C mutation (1% of total). These mutants were chosen due to their likely different mode of interaction with JAK2 inhibitors. Under these conditions, neither mutation could be detected by sequencing of the genomic DNA at the beginning of the assay (FIG. 3A, top panel). Subsequently, cells were grown for seven days in the presence of solvent (DMSO) or ruxolitinib (300 nM). Previous experiments suggest that this concentration is sufficient to significantly, but not completely, impair viability and cell growth (FIG. 2A) in parental cells, whereas mutant expressing cells are unaffected in a three day culture. Sequencing of genomic DNA revealed that seven days after treatment with ruxolitinib, more than half of the sequence material contained the E985K or Y931C mutation, but not the control treated cells (FIG. 3A, bottom panel).

Immunoblotting

Immunoblotting was performed using a standard chemiluminescence technique, as described previously. Rabbit polyclonal antibodies against STAT5 (Santa Cruz Biotechnology, Santa Cruz, Calif.), phospho-STAT5 (Y694—Cell Signaling, Danvers, Mass.) or a mouse monoclonal antibody against β-actin (AC-15; Sigma) were used.

The efficacy of ruxolitinib at this concentration was also confirmed by measuring changes in phosphorylation of the JAK2 target STAT5 by immunoblotting. Ruxolitinib failed to inhibit phosphorylation of STAT5 at its activation site in both of the resistant cell lines, but not in JAK2V617F expressing cells (FIG. 3B). These data would support the findings that both mutations specifically cause ruxolitinib resistance at low doses.

Example 5. The 'Gatekeeper' M929I Mutation Specifically Alters Ruxolitinib Sensitivity Previously, mutations of the so called 'gatekeeper' site in the hinge region of various tyrosine kinases, including ABL (T315), EGFR (T790), KIT (T670) and PDGFRα (T674), were associated with strong in vitro and in vivo resistance to their respective inhibitors. However, the screen did not reveal prominent mutations at this site that could be detected with the approach described herein. Structural analysis and sequence alignment (Table 1) indicate that M929 in human and murine JAK2 is homologous to the T315I gatekeeper site in ABL and other tyrosine kinases. In these kinases the valine or threonine residues were commonly mutated into either isoleucine or methionine. In JAK2, this site already contained a methionine residue in the 'gatekeeper' position and we therefore mutated it into isoleucine. Similar to the experiments above, the dose dependent reduction in growth in response to various JAK2 inhibitors and calculated EC50 values was determined (FIG. 3C). As expected, no change in sensitivity of the M929I mutation towards CYT-387, TG101348, AZD1480 or lestaurtinib was observed. Interestingly, this assay demonstrated that the M929I mutation only displayed resistance to ruxolitinib (4.3-fold increase in EC50). The sidechain of M929 does not have apparent polar contacts with ruxolitinib, but is at the far end of the hydrophobic groove that binds the kinase inhibitors and may influence the correct positioning of the drug in the hydrophobic binding pocket.

TABLE 1

| | | | | | | | | | | | | | | | | | | | |
|---|---|---|---|---|---|---|---|---|---|---|---|---|---|---|---|---|---|---|---|
| KIT | P | T | L | V | I | $T^{670}$ | E | Y | C | C | Y | G | D | L | L | N | F | L | R | (SEQ ID NO: 6) $T670I^{23}$ |
| PDGFRα | P | I | Y | I | I | $T^{674}$ | E | Y | C | F | Y | G | D | L | V | N | Y | L | H | (SEQ ID NO: 7) $T674I^{19}$ |
| hJAK2 | N | L | K | L | I | $M^{929}$ | E | Y | L | P | Y | G | S | L | R | D | Y | L | Q | (SEQ ID NO: 8) |
| mJAK2 | N | L | R | L | I | $M^{929}$ | E | Y | L | P | Y | G | S | L | R | D | Y | L | Q | (SEQ ID NO: 9) |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of treating a subject having a myeloproliferative malignancy comprising:
   a) detecting the absence of one or more point mutations selected from the group consisting of R938L, I960V, and E985K in the kinase domain of the JAK2V617F polypeptide in a biological sample obtained from the subject;
   b) diagnosing the subject as responsive to a JAK inhibitor selected from the group consisting of ruxolitinib, CYT-387, TG101348, AZD1480, and lestaurtinib; and
   c) administering the JAK inhibitor to the subject diagnosed to be responsive to the JAK inhibitor.

2. The method of claim 1, wherein the myeloproliferative malignancy is polycythemia vera, essential thrombocythemia, idiopathic myelofibrosis, acute myeloid leukemia, or myelodysplastic syndrome.

3. The method of claim 1, further comprising detecting the absence of point mutation Y931C or G935R.

4. The method of claim 1, wherein the subject is a mammal.

5. The method of claim 1, wherein the subject is a human.

6. The method of claim 1, wherein the biological sample is a tissue biopsy, whole blood, serum, plasma, saliva, or urine.

7. The method of claim 6, wherein the biological sample is whole blood, serum, or plasma.

8. The method of claim 1, wherein the method alleviates the symptoms of the myeloproliferative malignancy.

9. The method of claim 1, wherein the subject is asymptomatic for cancer recurrence.

10. The method of claim 1, wherein step (a) comprises using a mutant polypeptide-specific antibody that specifically binds to JAK2V617F with a mutation at amino acid position 938, 960, or 985.

11. The method of claim 1, wherein step (a) comprises using polymerase chain reaction.

* * * * *

SEQUENCE LISTING

<160> NUMBER OF SEQ ID NOS: 20

<210> SEQ ID NO 1
<211> LENGTH: 3652
<212> TYPE: DNA
<213> ORGANISM: Homo sapiens

<400> SEQUENCE: 1

```
tttctcttct gcagaaaaag aggctcttcc tcctcctccc gcgacggcaa atgttctgaa      60
aaagactctg catgggaatg gcctgcctta cgatgacaga aatggaggga acatccacct     120
cttctatata tcagaatggt gatatttctg gaaatgccaa ttctatgaag caaatagatc     180
cagttcttca ggtgtatctt taccattccc ttgggaaatc tgaggcagat tatctgacct     240
ttccatctgg ggagtatgtt gcagaagaaa tctgtattgc tgcttctaaa gcttgtggta     300
tcacacctgt gtatcataat atgtttgctt taatgagtga aacagaaagg atctggtatc     360
cacccaacca tgtcttccat atagatgagt caaccaggca taatgtactc tacagaataa     420
gattttactt tcctcgttgg tattgcagtg gcagcaacag agcctatcgg catggaatat     480
ctcgaggtgc tgaagctcct ctttcttgatg actttgtcat gtcttacctc tttgctcagt     540
ggcggcatga ttttgtgcac ggatggataa aagtacctgt gactcatgaa acacaggaag     600
```

```
aatgtcttgg gatggcagtg ttagatatga tgagaatagc caaagaaaac gatcaaaccc      660
cactggccat ctataactct atcagctaca agacattctt accaaaatgt attcgagcaa      720
agatccaaga ctatcatatt ttgacaagga agcgaataag gtacagattt cgcagattta      780
ttcagcaatt cagccaatgc aaagccactg ccagaaactt gaaacttaag tatcttataa      840
atctggaaac tctgcagtct gccttctaca cagagaaatt tgaagtaaaa gaacctggaa      900
gtggtccttc aggtgaggag attttttgcaa ccattataat aactggaaac ggtgaattc      960 agtggtcaag agggaaacat aaagaaagtg agacactgac agaacaggat ttacagttat     1020
attgcgattt tcctaatatt attgatgtca gtattaagca agcaaaccaa gagggttcaa     1080
atgaaagccg agttgtaact atccataagc aagatggtaa aaatctggaa attgaactta     1140
gctcattaag ggaagctttg tctttcgtgt cattaattga tggatattat agattaactg     1200
cagatgcaca tcattacctc tgtaaagaag tagcacctcc agccgtgctt gaaaatatac     1260
aaagcaactg tcatggccca atttcgatgg attttgccat tagtaaactg aagaaagcag     1320
gtaatcagac tggactgtat gtacttcgat gcagtcctaa ggactttaat aaatattttt     1380
tgacttttgc tgtcgagcga gaaaatgtca ttgaatataa acactgtttg attacaaaaa     1440
atgagaatga agagtacaac ctcagtggga caaagaagaa cttcagcagt cttaaagatc     1500
ttttgaattg ttaccagatg gaaactgttc gctcagacaa tataattttc cagtttacta     1560
aatgctgtcc cccaaagcca aaagataaat caaaccttct agtcttcaga acgaatggtg     1620
tttctgatgt accaacctca ccaacattac agaggcctac tcatatgaac caaatggtgt     1680
ttcacaaaat cagaaatgaa gatttgatat ttaatgaaag ccttggccaa ggcactttta     1740
caaagatttt taaggcgta cgaagagaag taggagacta cggtcaactg catgaaacag     1800
aagttctttt aaaagttctg gataaagcac acagaaacta ttcagagtct ttctttgaag     1860
cagcaagtat gatgagcaag ctttctcaca agcatttggt tttaaattat ggagtatgtt     1920
tctgtggaga cgagaatatt ctggttcagg agttttgtaaa atttggatca ctagatacat     1980
atctgaaaaa gaataaaaat tgtataaata tattatggaa acttgaagtt gctaaacagt     2040
tggcatgggc catgcatttt ctagaagaaa acacccttat tcatgggaat gtatgtgcca     2100
aaaatattct gcttatcaga gaagaagaca ggaagacagg aaatcctcct ttcatcaaac     2160
ttagtgatcc tggcattagt attacagttt tgccaaagga cattcttcag gagagaatac     2220
catgggtacc acctgaatgc attgaaaatc ctaaaaattt aaatttggca acagacaaat     2280
ggagttttgg taccactttg tgggaaatct gcagtggagg agataaaacct ctaagtgctc     2340 tggattctca aagaaagcta caatttttatg aagataggca tcagcttcct gcaccaaagt     2400
gggcagaatt agcaaccctt ataaataatt gtatggatta tgaaccagat ttcaggcctt     2460 cttttcagagc catcatacga gatcttaaca gtttgtttac tccagattat gaactattaa     2520
cagaaaatga catgttacca aatatgagga taggtgccct ggggttttct ggtgcctttg     2580
aagaccggga tcctacacag tttgaagaga gacatttgaa atttctacag caacttggca     2640
agggtaattt tgggagtgtg gagatgtgcc ggtatgaccc tctacaggac aacactgggg     2700
aggtggtcgc tgtaaaaaag cttcagcata gtactgaaga gcacctaaga gactttgaaa     2760
gggaaattga aatcctgaaa tccctacagc atgacaacat tgtaaagtac aagggagtgt     2820
gctacagtgc tggtcggcgt aatctaaaat taattatgga atattttcca tatggaagtt     2880
tacgagacta tcttcaaaaa cataaagaac ggatagatca cataaaactt ctgcagtaca     2940
catctcagat atgcaagggt atggagtatc ttggtacaaa aaggtatatc cacagggatc     3000
```

-continued

```
tggcaacgag aaatatattg gtggagaacg agaacagagt taaaattgga gattttgggt   3060
taaccaaagt cttgccacaa gacaaagaat actataaagt aaaagaacct ggtgaaagtc   3120
ccatattctg gtatgctcca gaatcactga cagagagcaa gttttctgtg gcctcagatg   3180
tttggagctt tggagtggtt ctgtatgaac ttttcacata cattgagaag agtaaaagtc   3240
caccagcgga atttatgcgt atgattggca atgacaaaca aggacagatg atcgtgttcc   3300
atttgataga acttttgaag aataatgaaa gattaccaag accagatgga tgcccagatg   3360
agatctatat gatcatgaca gaatgctgga acaataatgt aaatcaacgc ccctccttta   3420
gggatctagc tcttcgagtg gatcaaataa gggataacat ggctggatga agaaatgac    3480 cttcattctg agaccaaagt agatttacag aacaaagttt tatatttcac attgctgtgg   3540
actattatta catatatcat tattatataa atcatgatgc tagccagcaa agatgtgaaa   3600
atatctgctc aaaactttca agtttagta agttttctt catgaggcca cc            3652
```

```
<210> SEQ ID NO 2
<211> LENGTH: 1132
<212> TYPE: PRT
<213> ORGANISM: Homo sapiens

<400> SEQUENCE: 2

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
                20                  25                  30

Lys Gln Ile Asp Pro Val Leu Gln Val Tyr Leu Tyr His Ser Leu Gly
            35                  40                  45

Lys Ser Glu Ala Asp Tyr Leu Thr Phe Pro Ser Gly Glu Tyr Val Ala
        50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255
```

Asn Leu Glu Thr Leu Gln Ser Ala Phe Tyr Thr Glu Lys Phe Val
            260                 265                 270
Lys Glu Pro Gly Ser Gly Pro Ser Gly Glu Glu Ile Phe Ala Thr Ile
        275                 280                 285
Ile Ile Thr Gly Asn Gly Gly Ile Gln Trp Ser Arg Gly Lys His Lys
    290                 295                 300
Glu Ser Glu Thr Leu Thr Glu Gln Asp Leu Gln Leu Tyr Cys Asp Phe
305                 310                 315                 320
Pro Asn Ile Ile Asp Val Ser Ile Lys Gln Ala Asn Gln Glu Gly Ser
                325                 330                 335
Asn Glu Ser Arg Val Val Thr Ile His Lys Gln Asp Gly Lys Asn Leu
            340                 345                 350
Glu Ile Glu Leu Ser Ser Leu Arg Glu Ala Leu Ser Phe Val Ser Leu
        355                 360                 365
Ile Asp Gly Tyr Tyr Arg Leu Thr Ala Asp Ala His His Tyr Leu Cys
    370                 375                 380
Lys Glu Val Ala Pro Pro Ala Val Leu Glu Asn Ile Gln Ser Asn Cys
385                 390                 395                 400
His Gly Pro Ile Ser Met Asp Phe Ala Ile Ser Lys Leu Lys Lys Ala
                405                 410                 415
Gly Asn Gln Thr Gly Leu Tyr Val Leu Arg Cys Ser Pro Lys Asp Phe
            420                 425                 430
Asn Lys Tyr Phe Leu Thr Phe Ala Val Glu Arg Glu Asn Val Ile Glu
        435                 440                 445
Tyr Lys His Cys Leu Ile Thr Lys Asn Glu Asn Glu Glu Tyr Asn Leu
    450                 455                 460
Ser Gly Thr Lys Lys Asn Phe Ser Ser Leu Lys Asp Leu Leu Asn Cys
465                 470                 475                 480
Tyr Gln Met Glu Thr Val Arg Ser Asp Asn Ile Ile Phe Gln Phe Thr
                485                 490                 495
Lys Cys Cys Pro Pro Lys Pro Lys Asp Lys Ser Asn Leu Leu Val Phe
            500                 505                 510
Arg Thr Asn Gly Val Ser Asp Val Pro Thr Ser Pro Thr Leu Gln Arg
        515                 520                 525
Pro Thr His Met Asn Gln Met Val Phe His Lys Ile Arg Asn Glu Asp
    530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Glu Thr
                565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Lys Leu Ser His Lys His
        595                 600                 605
Leu Val Leu Asn Tyr Gly Val Cys Phe Cys Gly Asp Glu Asn Ile Leu
    610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
                645                 650                 655
Leu Ala Trp Ala Met His Phe Leu Glu Glu Asn Thr Leu Ile His Gly
            660                 665                 670
Asn Val Cys Ala Lys Asn Ile Leu Leu Ile Arg Glu Glu Asp Arg Lys

```
              675                 680                 685
Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val  Leu Pro Gln Asp Lys  Glu Tyr Tyr
        995                 1000                1005

Lys Val  Lys Glu Pro Gly Glu  Ser Pro Ile Phe Trp  Tyr Ala Pro
    1010                1015                1020

Glu Ser  Leu Thr Glu Ser Lys  Phe Ser Val Ala Ser  Asp Val Trp
    1025                1030                1035

Ser Phe  Gly Val Val Leu Tyr  Glu Leu Phe Thr Tyr  Ile Glu Lys
    1040                1045                1050

Ser Lys  Ser Pro Pro Ala Glu  Phe Met Arg Met Ile  Gly Asn Asp
    1055                1060                1065

Lys Gln  Gly Gln Met Ile Val  Phe His Leu Ile Glu  Leu Leu Lys
    1070                1075                1080

Asn Asn  Gly Arg Leu Pro Arg  Pro Asp Gly Cys Pro  Asp Glu Ile
    1085                1090                1095
```

-continued

```
Tyr Met Ile Met Thr Glu Cys Trp Asn Asn Asn Val Asn Gln Arg
    1100            1105                1110
Pro Ser Phe Arg Asp Leu Ala Leu Arg Val Asp Gln Ile Arg Asp
    1115            1120                1125
Asn Met Ala Gly
    1130

<210> SEQ ID NO 3
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 3
atgagccaga tttcaggcct gctt                                          24

<210> SEQ ID NO 4
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 4
agaaagttgg gcatcacgca gcta                                          24

<210> SEQ ID NO 5
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 5
acatgagaat aggtgcccta gg                                            22

<210> SEQ ID NO 6
<211> LENGTH: 19
<212> TYPE: PRT
<213> ORGANISM: Homo sapiens

<400> SEQUENCE: 6

Pro Thr Leu Val Ile Thr Glu Tyr Cys Cys Tyr Gly Asp Leu Leu Asn
1               5                   10                  15
Phe Leu Arg

<210> SEQ ID NO 7
<211> LENGTH: 19
<212> TYPE: PRT
<213> ORGANISM: Homo sapiens

<400> SEQUENCE: 7

Pro Ile Tyr Ile Ile Thr Glu Tyr Cys Phe Tyr Gly Asp Leu Val Asn
1               5                   10                  15
Tyr Leu His

<210> SEQ ID NO 8
<211> LENGTH: 19
<212> TYPE: PRT
<213> ORGANISM: Homo sapiens

<400> SEQUENCE: 8
```

Asn Leu Lys Leu Ile Met Glu Tyr Leu Pro Tyr Gly Ser Leu Arg Asp
1               5                   10                  15

Tyr Leu Gln

<210> SEQ ID NO 9
<211> LENGTH: 19
<212> TYPE: PRT
<213> ORGANISM: Homo sapiens

<400> SEQUENCE: 9

Asn Leu Arg Leu Ile Met Glu Tyr Leu Pro Tyr Gly Ser Leu Arg Asp
1               5                   10                  15

Tyr Leu Gln

<210> SEQ ID NO 10
<211> LENGTH: 11
<212> TYPE: DNA
<213> ORGANISM: Homo sapiens

<400> SEQUENCE: 10
tggtggaaaa t                                                        11

<210> SEQ ID NO 11
<211> LENGTH: 10
<212> TYPE: DNA
<213> ORGANISM: Homo sapiens

<400> SEQUENCE: 11
ggaatattac                                                          10

<210> SEQ ID NO 12
<211> LENGTH: 10
<212> TYPE: DNA
<213> ORGANISM: Homo sapiens

<400> SEQUENCE: 12
tggtggaaat                                                          10

<210> SEQ ID NO 13
<211> LENGTH: 11
<212> TYPE: DNA
<213> ORGANISM: Homo sapiens

<400> SEQUENCE: 13
ggaatattta c                                                        11

<210> SEQ ID NO 14
<211> LENGTH: 11
<212> TYPE: DNA
<213> ORGANISM: Homo sapiens

<400> SEQUENCE: 14
tggtgraaaa t                                                        11

<210> SEQ ID NO 15
<211> LENGTH: 11
<212> TYPE: DNA
<213> ORGANISM: Homo sapiens

<400> SEQUENCE: 15
ggaatrttta c                                                        11

<210> SEQ ID NO 16
<211> LENGTH: 1132
<212> TYPE: PRT
<213> ORGANISM: Homo sapiens

<400> SEQUENCE: 16

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
    370                 375                 380
```

```
Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
            405                 410                 415

Gly Asn Gln Thr Gly Leu Tyr Val Leu Arg Cys Ser Pro Lys Asp Phe
        420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
        450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
        515                 520                 525

Pro Thr His Met Asn Gln Met Val Phe His Lys Ile Arg Asn Glu Asp
        530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Lys Leu Ser His Lys His
        595                 600                 605

Leu Val Leu Asn Tyr Gly Val Cys Phe Cys Gly Asp Glu Asn Ile Leu
        610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670

Asn Val Cys Ala Lys Asn Ile Leu Leu Ile Arg Glu Glu Asp Arg Lys
        675                 680                 685

Thr Gly Asn Pro Pro Phe Ile Lys Leu Ser Asp Pro Gly Ile Ser Ile
        690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
        770                 775                 780

Asn Asn Cys Met Asp Tyr Glu Pro Asp Phe Arg Pro Ser Phe Arg Ala
785                 790                 795                 800
```

```
Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Cys Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile
    1085                1090                1095

Tyr Met Ile Met Thr Glu Cys Trp Asn Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 17
<211> LENGTH: 1132
<212> TYPE: PRT
<213> ORGANISM: Homo sapiens

<400> SEQUENCE: 17

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30
```

```
Lys Gln Ile Asp Pro Val Leu Gln Val Tyr Leu Tyr His Ser Leu Gly
         35                  40                  45

Lys Ser Glu Ala Asp Tyr Leu Thr Phe Pro Ser Gly Glu Tyr Val Ala
     50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                     85                  90                  95

Pro Pro Asn His Val Phe His Ile Asp Glu Ser Thr Arg His Asn Val
             100                 105                 110

Leu Tyr Arg Ile Arg Phe Tyr Phe Pro Arg Trp Tyr Cys Ser Gly Ser
             115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                 165                 170                 175

Glu Cys Leu Gly Met Ala Val Leu Asp Met Met Arg Ile Ala Lys Glu
             180                 185                 190

Asn Asp Gln Thr Pro Leu Ala Ile Tyr Asn Ser Ile Ser Tyr Lys Thr
             195                 200                 205

Phe Leu Pro Lys Cys Ile Arg Ala Lys Ile Gln Asp Tyr His Ile Leu
210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                 245                 250                 255

Asn Leu Glu Thr Leu Gln Ser Ala Phe Tyr Thr Glu Lys Phe Glu Val
             260                 265                 270

Lys Glu Pro Gly Ser Gly Pro Ser Gly Glu Glu Ile Phe Ala Thr Ile
             275                 280                 285

Ile Ile Thr Gly Asn Gly Gly Ile Gln Trp Ser Arg Gly Lys His Lys
         290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                 325                 330                 335

Asn Glu Ser Arg Val Val Thr Ile His Lys Gln Asp Gly Lys Asn Leu
             340                 345                 350

Glu Ile Glu Leu Ser Ser Leu Arg Glu Ala Leu Ser Phe Val Ser Leu
             355                 360                 365

Ile Asp Gly Tyr Tyr Arg Leu Thr Ala Asp Ala His His Tyr Leu Cys
         370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                 405                 410                 415

Gly Asn Gln Thr Gly Leu Tyr Val Leu Arg Cys Ser Pro Lys Asp Phe
             420                 425                 430

Asn Lys Tyr Phe Leu Thr Phe Ala Val Glu Arg Glu Asn Val Ile Glu
             435                 440                 445
```

```
Tyr Lys His Cys Leu Ile Thr Lys Asn Glu Asn Glu Glu Tyr Asn Leu
    450                 455                 460
Ser Gly Thr Lys Lys Asn Phe Ser Ser Leu Lys Asp Leu Leu Asn Cys
465                 470                 475                 480
Tyr Gln Met Glu Thr Val Arg Ser Asp Asn Ile Ile Phe Gln Phe Thr
                485                 490                 495
Lys Cys Cys Pro Pro Lys Pro Lys Asp Lys Ser Asn Leu Leu Val Phe
                500                 505                 510
Arg Thr Asn Gly Val Ser Asp Val Pro Thr Ser Pro Thr Leu Gln Arg
            515                 520                 525
Pro Thr His Met Asn Gln Met Val Phe His Lys Ile Arg Asn Glu Asp
530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Glu Thr
                565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Lys Leu Ser His Lys His
            595                 600                 605
Leu Val Leu Asn Tyr Gly Val Cys Phe Cys Gly Asp Glu Asn Ile Leu
610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
                645                 650                 655
Leu Ala Trp Ala Met His Phe Leu Glu Glu Asn Thr Leu Ile His Gly
            660                 665                 670
Asn Val Cys Ala Lys Asn Ile Leu Leu Ile Arg Glu Glu Asp Arg Lys
            675                 680                 685
Thr Gly Asn Pro Pro Phe Ile Lys Leu Ser Asp Pro Gly Ile Ser Ile
    690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
                725                 730                 735
Trp Ser Phe Gly Thr Thr Leu Trp Glu Ile Cys Ser Gly Gly Asp Lys
            740                 745                 750
Pro Leu Ser Ala Leu Asp Ser Gln Arg Lys Leu Gln Phe Tyr Glu Asp
            755                 760                 765
Arg His Gln Leu Pro Ala Pro Lys Trp Ala Glu Leu Ala Asn Leu Ile
    770                 775                 780
Asn Asn Cys Met Asp Tyr Glu Pro Asp Phe Arg Pro Ser Phe Arg Ala
785                 790                 795                 800
Ile Ile Arg Asp Leu Asn Ser Leu Phe Thr Pro Asp Tyr Glu Leu Leu
                805                 810                 815
Thr Glu Asn Asp Met Leu Pro Asn Met Arg Ile Gly Ala Leu Gly Phe
            820                 825                 830
Ser Gly Ala Phe Glu Asp Arg Asp Pro Thr Gln Phe Glu Glu Arg His
            835                 840                 845
Leu Lys Phe Leu Gln Gln Leu Gly Lys Gly Asn Phe Gly Ser Val Glu
    850                 855                 860
Met Cys Arg Tyr Asp Pro Leu Gln Asp Asn Thr Gly Glu Val Val Ala
```

```
            865                 870                 875                 880
        Val Lys Lys Leu Gln His Ser Thr Glu Glu His Leu Arg Asp Phe Glu
                        885                 890                 895

Arg Glu Ile Glu Ile Leu Lys Ser Leu Gln His Asp Asn Ile Val Lys
                        900                 905                 910

Tyr Lys Gly Val Cys Tyr Ser Ala Gly Arg Arg Asn Leu Lys Leu Ile
                        915                 920                 925

Met Glu Tyr Leu Pro Tyr Arg Ser Leu Arg Asp Tyr Leu Gln Lys His
                        930                 935                 940

Lys Glu Arg Ile Asp His Ile Lys Leu Leu Gln Tyr Thr Ser Gln Ile
        945                 950                 955                 960

Cys Lys Gly Met Glu Tyr Leu Gly Thr Lys Arg Tyr Ile His Arg Asp
                        965                 970                 975

Leu Ala Thr Arg Asn Ile Leu Val Glu Asn Gly Asn Arg Val Lys Ile
                        980                 985                 990

Gly Asp Phe Gly Leu Thr Lys Val Leu Pro Gln Asp Lys Glu Tyr Tyr
                        995                 1000                1005

Lys Val Lys Glu Pro Gly Glu Ser Pro Ile Phe Trp Tyr Ala Pro
                  1010                1015                1020

Glu Ser Leu Thr Glu Ser Lys Phe Ser Val Ala Ser Asp Val Trp
                  1025                1030                1035

Ser Phe Gly Val Val Leu Tyr Glu Leu Phe Thr Tyr Ile Glu Lys
                  1040                1045                1050

Ser Lys Ser Pro Pro Ala Glu Phe Met Arg Met Ile Gly Asn Asp
                  1055                1060                1065

Lys Gln Gly Gln Met Ile Val Phe His Leu Ile Glu Leu Leu Lys
                  1070                1075                1080

Asn Asn Gly Arg Leu Pro Arg Pro Asp Gly Cys Pro Asp Glu Ile
                  1085                1090                1095

Tyr Met Ile Met Thr Glu Cys Trp Asn Asn Val Asn Gln Arg
                  1100                1105                1110

Pro Ser Phe Arg Asp Leu Ala Leu Arg Val Asp Gln Ile Arg Asp
                  1115                1120                1125

Asn Met Ala Gly
                  1130

<210> SEQ ID NO 18
<211> LENGTH: 1132
<212> TYPE: PRT
<213> ORGANISM: Homo sapiens

<400> SEQUENCE: 18

Met Gly Met Ala Cys Leu Thr Met Thr Glu Met Glu Gly Thr Ser Thr
        1               5                   10                  15

Ser Ser Ile Tyr Gln Asn Gly Asp Ile Ser Gly Asn Ala Asn Ser Met
                        20                  25                  30

Lys Gln Ile Asp Pro Val Leu Gln Val Tyr Leu Tyr His Ser Leu Gly
                        35                  40                  45

Lys Ser Glu Ala Asp Tyr Leu Thr Phe Pro Ser Gly Glu Tyr Val Ala
                        50                  55                  60

Glu Glu Ile Cys Ile Ala Ala Ser Lys Ala Cys Gly Ile Thr Pro Val
        65                  70                  75                  80

Tyr His Asn Met Phe Ala Leu Met Ser Glu Thr Glu Arg Ile Trp Tyr
                        85                  90                  95
```

-continued

```
Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Phe Ile Gln Gln Phe
225                 230                 235                 240

Ser Gln Cys Lys Ala Thr Ala Arg Asn Leu Lys Leu Lys Tyr Leu Ile
            245                 250                 255

Asn Leu Glu Thr Leu Gln Ser Ala Phe Tyr Thr Glu Lys Phe Glu Val
        260                 265                 270

Lys Glu Pro Gly Ser Gly Pro Ser Gly Glu Glu Ile Phe Ala Thr Ile
    275                 280                 285

Ile Ile Thr Gly Asn Gly Gly Ile Gln Trp Ser Arg Gly Lys His Lys
290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
            325                 330                 335

Asn Glu Ser Arg Val Val Thr Ile His Lys Gln Asp Gly Lys Asn Leu
        340                 345                 350

Glu Ile Glu Leu Ser Ser Leu Arg Glu Ala Leu Ser Phe Val Ser Leu
    355                 360                 365

Ile Asp Gly Tyr Tyr Arg Leu Thr Ala Asp Ala His His Tyr Leu Cys
370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
            405                 410                 415

Gly Asn Gln Thr Gly Leu Tyr Val Leu Arg Cys Ser Pro Lys Asp Phe
        420                 425                 430

Asn Lys Tyr Phe Leu Thr Phe Ala Val Glu Arg Glu Asn Val Ile Glu
    435                 440                 445

Tyr Lys His Cys Leu Ile Thr Lys Asn Glu Asn Glu Tyr Asn Leu
450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
            485                 490                 495

Lys Cys Cys Pro Pro Lys Pro Lys Asp Lys Ser Asn Leu Leu Val Phe
        500                 505                 510

Arg Thr Asn Gly Val Ser Asp Val Pro Thr Ser Pro Thr Leu Gln Arg
```

```
                515                 520                 525
Pro Thr His Met Asn Gln Met Val Phe His Lys Ile Arg Asn Glu Asp
530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
                580                 585                 590

Ser Phe Phe Glu Ala Ala Ser Met Met Ser Lys Leu Ser His Lys His
                595                 600                 605

Leu Val Leu Asn Tyr Gly Val Cys Phe Cys Gly Asp Glu Asn Ile Leu
610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
                660                 665                 670

Asn Val Cys Ala Lys Asn Ile Leu Leu Ile Arg Glu Asp Arg Lys
                675                 680                 685

Thr Gly Asn Pro Pro Phe Ile Lys Leu Ser Asp Pro Gly Ile Ser Ile
690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
                740                 745                 750

Pro Leu Ser Ala Leu Asp Ser Gln Arg Lys Leu Gln Phe Tyr Glu Asp
                755                 760                 765

Arg His Gln Leu Pro Ala Pro Lys Trp Ala Glu Leu Ala Asn Leu Ile
770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
                820                 825                 830

Ser Gly Ala Phe Glu Asp Arg Asp Pro Thr Gln Phe Glu Glu Arg His
                835                 840                 845

Leu Lys Phe Leu Gln Gln Leu Gly Lys Gly Asn Phe Gly Ser Val Glu
                850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
                900                 905                 910

Tyr Lys Gly Val Cys Tyr Ser Ala Gly Arg Arg Asn Leu Lys Leu Ile
                915                 920                 925

Met Glu Tyr Leu Pro Tyr Gly Ser Leu Leu Asp Tyr Leu Gln Lys His
                930                 935                 940
```

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile
    1085                1090                1095

Tyr Met Ile Met Thr Glu Cys Trp Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 19
<211> LENGTH: 1132
<212> TYPE: PRT
<213> ORGANISM: Homo sapiens

<400> SEQUENCE: 19

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu

```
                165                 170                 175
Glu Cys Leu Gly Met Ala Val Leu Asp Met Met Arg Ile Ala Lys Glu
                180                 185                 190

Asn Asp Gln Thr Pro Leu Ala Ile Tyr Asn Ser Ile Ser Tyr Lys Thr
                195                 200                 205

Phe Leu Pro Lys Cys Ile Arg Ala Lys Ile Gln Asp Tyr His Ile Leu
            210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
                340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
    370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
                420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
        450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
                500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
        530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
            580                 585                 590
```

```
Ser Phe Phe Glu Ala Ala Ser Met Met Ser Lys Leu Ser His Lys His
        595                 600                 605

Leu Val Leu Asn Tyr Gly Val Cys Phe Cys Gly Asp Glu Asn Ile Leu
    610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670

Asn Val Cys Ala Lys Asn Ile Leu Leu Ile Arg Glu Gly Asp Arg Lys
        675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Val
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val  Leu Pro Gln Asp Lys  Glu Tyr Tyr
        995                  1000                1005
```

-continued

```
Lys Val Lys Glu Pro Gly Glu Ser Pro Ile Phe Trp Tyr Ala Pro
1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile
    1085                1090                1095

Tyr Met Ile Met Thr Glu Cys Trp Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 20
<211> LENGTH: 1132
<212> TYPE: PRT
<213> ORGANISM: Homo sapiens

<400> SEQUENCE: 20

Met Gly Met Ala Cys Leu Thr Met Thr Glu Met Glu Gly Thr Ser
1               5                   10                  15

Ser Ser Ile Tyr Gln Asn Gly Asp Ile Ser Gly Asn Ala Asn Ser Met
                20                  25                  30

Lys Gln Ile Asp Pro Val Leu Gln Val Tyr Leu Tyr His Ser Leu Gly
                35                  40                  45

Lys Ser Glu Ala Asp Tyr Leu Thr Phe Pro Ser Gly Glu Tyr Val Ala
50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
                100                 105                 110

Leu Tyr Arg Ile Arg Phe Tyr Phe Pro Arg Trp Tyr Cys Ser Gly Ser
                115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
                180                 185                 190

Asn Asp Gln Thr Pro Leu Ala Ile Tyr Asn Ser Ile Ser Tyr Lys Thr
                195                 200                 205

Phe Leu Pro Lys Cys Ile Arg Ala Lys Ile Gln Asp Tyr His Ile Leu
                210                 215                 220

Thr Arg Lys Arg Ile Arg Tyr Arg Phe Arg Arg Phe Ile Gln Gln Phe
225                 230                 235                 240
```

-continued

Ser Gln Cys Lys Ala Thr Ala Arg Asn Leu Lys Leu Lys Tyr Leu Ile
            245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
            325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
            370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
            405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
            450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
            485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
            565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Lys Leu Ser His Lys His
            595                 600                 605

Leu Val Leu Asn Tyr Gly Val Cys Phe Cys Gly Asp Glu Asn Ile Leu
            610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
            645                 650                 655

```
Leu Ala Trp Ala Met His Phe Leu Glu Glu Asn Thr Leu Ile His Gly
            660                 665                 670

Asn Val Cys Ala Lys Asn Ile Leu Leu Ile Arg Glu Glu Asp Arg Lys
            675                 680                 685

Thr Gly Asn Pro Pro Phe Ile Lys Leu Ser Asp Pro Gly Ile Ser Ile
            690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
                740                 745                 750

Pro Leu Ser Ala Leu Asp Ser Gln Arg Lys Leu Gln Phe Tyr Glu Asp
                755                 760                 765

Arg His Gln Leu Pro Ala Pro Lys Trp Ala Glu Leu Ala Asn Leu Ile
            770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
                820                 825                 830

Ser Gly Ala Phe Glu Asp Arg Asp Pro Thr Gln Phe Glu Glu Arg His
            835                 840                 845

Leu Lys Phe Leu Gln Gln Leu Gly Lys Gly Asn Phe Gly Ser Val Glu
850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
            915                 920                 925

Met Glu Tyr Leu Pro Tyr Gly Ser Leu Arg Asp Tyr Leu Gln Lys His
            930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Lys Asn Glu Asn Arg Val Lys Ile
            980                 985                 990

Gly Asp Phe Gly Leu Thr Lys Val Leu Pro Gln Asp Lys Glu Tyr Tyr
            995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
```

|  |  |  |  |  |  |  |  |  |  |  |
|---|---|---|---|---|---|---|---|---|---|---|
| 1070 | | | | 1075 | | | | 1080 | | |
| Asn | Asn | Gly | Arg | Leu | Pro | Arg | Pro | Asp | Gly | Cys | Pro | Asp | Glu | Ile |
| | 1085 | | | | 1090 | | | | 1095 | |
| Tyr | Met | Ile | Met | Thr | Glu | Cys | Trp | Asn | Asn | Val | Asn | Gln | Arg |
| | 1100 | | | | 1105 | | | | 1110 | |
| Pro | Ser | Phe | Arg | Asp | Leu | Ala | Leu | Arg | Val | Asp | Gln | Ile | Arg | Asp |
| | 1115 | | | | 1120 | | | | 1125 | |
| Asn | Met | Ala | Gly |
| | 1130 | | |